(12) United States Patent
Nguyen-Kim et al.

(10) Patent No.: US 8,821,843 B2
(45) Date of Patent: Sep. 2, 2014

(54) RHEOLOGY MODIFYING AND SETTING POLYMER, COMPOSITION THEREOF AND METHOD FOR MAKING IT

(75) Inventors: Son Nguyen-Kim, Hemsbach (DE); Rolf Werner, Ludwigshafen (DE); Angelika Schmitt, Worms (DE); Peter Hossel, Schifferstadt (DE); Matthias Laubender, Schifferstadt (DE); Jens Schröder, Frankenthal (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/642,346

(22) PCT Filed: Apr. 28, 2011

(86) PCT No.: PCT/EP2011/056768
§ 371 (c)(1),
(2), (4) Date: Feb. 7, 2013

(87) PCT Pub. No.: WO2011/135039
PCT Pub. Date: Nov. 3, 2011

(65) Prior Publication Data
US 2013/0129658 A1    May 23, 2013

Related U.S. Application Data

(60) Provisional application No. 61/328,669, filed on Apr. 28, 2010.

(30) Foreign Application Priority Data

Apr. 28, 2010  (EP) .................................... 10161317

(51) Int. Cl.
| | | |
|---|---|---|
| *A61K 8/72* | (2006.01) | |
| *A61K 8/81* | (2006.01) | |
| *A61K 8/73* | (2006.01) | |
| *C08F 212/00* | (2006.01) | |
| *C08F 18/00* | (2006.01) | |
| *C08F 20/26* | (2006.01) | |
| *C08L 39/00* | (2006.01) | |
| *C08L 37/00* | (2006.01) | |
| *C08L 33/24* | (2006.01) | |
| *C08L 23/02* | (2006.01) | |
| *C08F 220/10* | (2006.01) | |
| *C09D 133/26* | (2006.01) | |
| *C08L 35/02* | (2006.01) | |
| *C08F 290/04* | (2006.01) | |
| *A61Q 5/06* | (2006.01) | |

(52) U.S. Cl.
CPC ............... *A61K 8/8158* (2013.01); *C08L 39/00* (2013.01); *A61K 8/8147* (2013.01); *C08L 37/00* (2013.01); *C08L 33/24* (2013.01); *C08L 23/02* (2013.01); *C08F 220/10* (2013.01); *C09D 133/26* (2013.01); *C08L 35/02* (2013.01); *A61K 2800/48* (2013.01); *C08F 290/04* (2013.01); *A61Q 5/06* (2013.01)
USPC ................... 424/70.11; 424/70.16; 424/70.17; 526/307.5; 526/320; 526/209

(58) Field of Classification Search
USPC .............. 424/70.11, 70.16, 70.17; 526/307.5, 526/320, 209
See application file for complete search history.

(56) References Cited

U.S. PATENT DOCUMENTS

| | | | |
|---|---|---|---|
| 5,936,026 A | 8/1999 | Huybrechts et al. | |
| 2006/0100351 A1 | 5/2006 | Butera et al. | |
| 2009/0162295 A1* | 6/2009 | Winter et al. ................... | 424/45 |
| 2010/0040573 A1* | 2/2010 | Garcia Castro et al. ... | 424/78.32 |

FOREIGN PATENT DOCUMENTS

| | | |
|---|---|---|
| EP | 1197536 | 4/2002 |
| WO | WO-94/21701 | 9/1994 |
| WO | WO-01/85865 | 11/2001 |
| WO | WO-03/061615 | 7/2003 |

OTHER PUBLICATIONS

Philipp, Burkart, et al., Polyelectrolyte Complexes—Recent Developments and Open Problems, *Prog. Polym. Sci.* vol. 14 1989, 91-172.

* cited by examiner

*Primary Examiner* — Abigail Fisher
(74) *Attorney, Agent, or Firm* — Servilla Whitney LLC

(57) ABSTRACT

The invention relates to a polymer suited for modifying the styling performance and the rheology of a cosmetic preparation, a composition thereof, a method of making it as well as the use of said polymer and the composition respectively. The copolymer comprises at least one non-ionic ethylenically unsaturated C1-C4 (meth)acrylate as monomer A; an ethylenically unsaturated monomer B having as hydrogen bond donor an amide group, said ethylenically unsaturated monomer B being an ethylenically unsaturated monomer having a cyclic amide moiety, as monomer B1 and/or, an ethylenically unsaturated monomer having an acyclic amide group, as monomer B2; at least one ethylenically unsaturated carboxylic acid as monomer C; a macromonomer D; optionally at least one cross-linker E; and optionally at least one further monomer F.

14 Claims, 1 Drawing Sheet

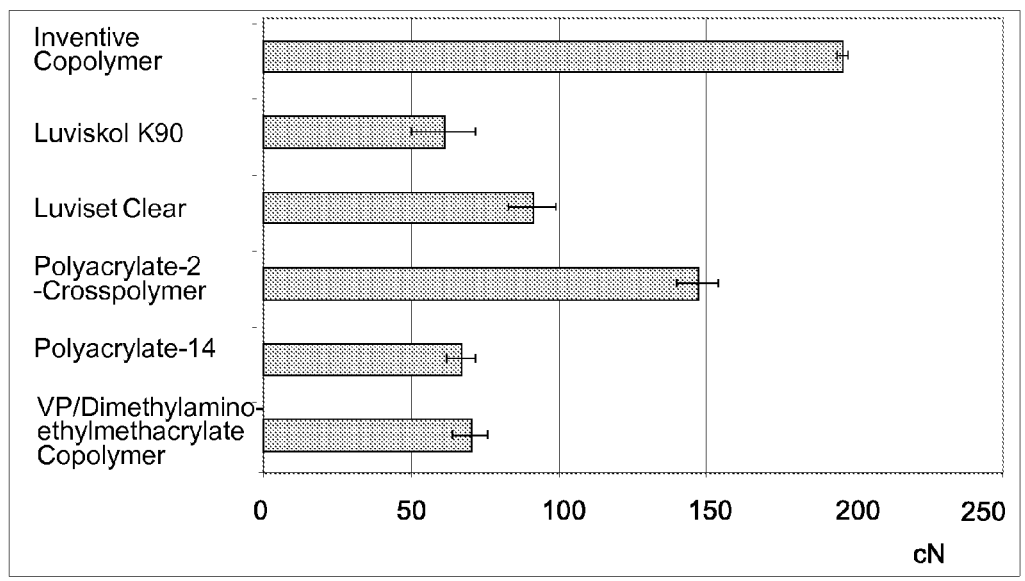

RHEOLOGY MODIFYING AND SETTING POLYMER, COMPOSITION THEREOF AND METHOD FOR MAKING IT

The invention relates to a polymer suited for modifying the styling performance in particular the setting performance and also the rheology of a cosmetic preparation, a composition of said polymer, a method of making it as well as the use of said polymer and the composition respectively.

The prior art knows already polymers having said properties. However, they suffer from some drawbacks which will be addressed by this invention Anionic water-soluble copolymers comprising associative monomers of the general structure $C_{12-22}$-alkyl-PEG-(M)A, with $C_{12-22}$-alkyl being an alkyl radical having 12 to 22 carbon atoms, PEG being a moiety comprising at least one $CH_2$—$CH_2$—O— group and (M)A representing acrylate or methacrylate, are known to be used in cosmetic formulations as rheology modifier. However, they are less qualified as hair setting means.

In addition several copolymers are known to give formulations which have a good hair setting performance. For instance copolymers comprising N-vinylpyrrolidone, methacrylamide and vinylimidazole commercialized under the tradename Luviset® Clear are suitable for hair gel formulations. However, they do not per se provide a pronounced rheology modifying capacity and have to be combined with thickener in a formulation. Since these copolymers have quite compact structures, their ability to be mixed with thickeners is not so pronounced thus requiring more thickener in a formulation which increases costs for a formulation.

In WO 03/061615 A1a huge quantity of different specimen of hair setting polymers is disclosed which they term rheology modifying hair styling polymers "RMHS polymers". Said RMHS polymers are prepared from a monomer mixture containing an acidic vinyl monomer, an associative monomer, and other monomers, such as nonionic vinyl monomers, cross-linking monomers, semi-hydrophobic monomers and chain transfer agents.

Said RMHS polymers can be further classified into hydrophobically modified alkali-swellable or alkali-soluble emulsion polymers, conventionally referred to as "HASE polymers" and into alkali-swellable or alkali-soluble associative polymers "ASAP polymers". The '615 discloses both of them.

HASE polymers are shown to be composed of an acidic vinyl monomer, a non-ionic vinyl monomer an associative monomer and other monomers, which are mostly crosslinkers. The associative monomer is beheneth-25 methacrylate or ceteareth-25 methacrylate or a mixture thereof, viz. a tripartite monomer consisting of a hydrophobic alkyl chain ether-linked to a polyethylene glycol having 25 methyleneoxy units and said polyethylene glycol is esterified with methacrylic acid. Said associative monomers are prone to make substantial hydrophobic interaction with other non-polar structures.

However, the HASE polymers disclosed do not provide any nitrogen-born hydrogen suitable to interact with the associative monomers by means of H-bridging, which both would have an impact on the polymer's setting performance as well as on its capacity to thicken compositions. Thus, the HASE polymers disclosed can still be improved in this regard.

ASAP polymers of the '615 are considered to make three classes. the first one comprises an acidic vinyl monomer, a non-ionic vinyl monomer, associative monomers and optional monomers. The second one is made of an acidic vinyl monomer, a non-ionic vinyl monomer, associative monomers, at least one semi-hydrophobic monomer "SH-monomer" and optional monomers. Finally the third one comprises an acidic vinyl monomer, a non-ionic vinyl monomer, associative monomers at least one semi-hydrophobic monomer "SH-monomer" and chain transfer agents provided for stopping polymerization.

All these ASAP polymers commonly require at least two associative monomers, or at least an associative monomer and a semi-hydrophobic monomer or at least an associative monomer and an optional monomer which is a cross-linker or a change transfer agent, or even a combination of associative monomer, semi-hydrophobic monomer and optional monomer.

This can be clearly seen from page 12 para 1 of the '615 where it reads: "In a preferred embodiment, the ASAP is the polymerization product of a monomer mixture comprising, on a total monomer mixture weight basis: (a) about 10 to about 75 weight percent of at least one acidic vinyl monomer or a salt thereof; (b) about 10 to about 90 weight percent of at least one nonionic vinyl monomer; (c) about 0.1 to about 25 weight percent of a first associative monomer having a first hydrophobic end group; (d) about 0.1 to about 25 weight percent of at least one monomer selected from the group consisting of a second associative monomer having a second hydrophobic end group, a semi-hydrophobic monomer and a combination thereof; and, optionally, (e) about 0.01 to about 20 weight percent of one or more monomers selected from the group consisting of a cross-linking monomer, a chain transfer agent, and a combination thereof."

This substantial amount of rather sophisticated monomers makes the polymer composition rather complicated and also expensive since most of the monomer types previously indicated are rather complex large-sized entities only affordable at a considerable price.

Furthermore, setting performance and thickening behaviour of these ASAP polymers on a molecular basis substantially relies on hydrophobic interactions and on the repulsion of neutralized carboxy groups of the acrylic acids used. This gives already a certain setting performance of the polymers disclosed in a cosmetic composition and also confers to these polymers a defined thickening capacity. However, these parameters are still to be optimized.

It is thus an object of the invention to provide new copolymers which increase the styling performance in compositions used for cosmetic purposes especially used in hair cosmetics. In particular these new polymers shall have extensive setting performance especially when being part of a hair styling composition and even more if said hair styling composition contains carbomer type thickeners. They also shall increase the rheology modifying capacity of thickening compositions or of cosmetic compositions. They further shall provide considerable viscosity values both when determined on the polymer per se and with a composition comprising the polymer of the invention. Said copolymers also shall improve compatibility between hair styling or setting copolymers and viscosity increasing agents. Making of these polymers shall be cost-effective and straight forward. Another object of the invention is to provide a rheology-modifying composition or a cosmetic composition comprising at least one polymer of the invention. Said composition preferably shall have a clear aspect. It shall have a viscosity equal or superior to 18.000 mPa and a pH ranging from 5 to 8. Said composition is required to have a rather homogeneous structure and to generate a good stiffening effect on hair on which it is applied. The stickiness and the sensory stickiness shall be acceptable and the composition of the invention is to be easily washed out from the wet hair. The composition comprising the polymer of the invention shall also provide a good flexural strength to treated hair and said treated hair shall have a high capacity to retain curls. Especially compositions are required having a polymer incorporated which both rises the styling performance of the composition viz. gives high values of curl retention and flexural strength and at the same time reduces the amount of additional thickener to be required in the composition since it also assumes part of thickener properties, viz. confers high viscosity values to the composition. In short said rheology-modifying composition should be cost-effective. Yet another object of the invention is to provide a process for making the polymer of the invention as well as its respective compositions. Such process shall be cost-effective and time saving. Finally another object of the invention is to pinpoint particular uses of the copolymer of the invention and of compositions thereof.

All these features can be addressed by a copolymer for rheological or cosmetic compositions comprising 15 to 60 w % of at least one non-ionic ethylenically unsaturated C1-C4 (meth)acrylate as monomer A; 0.1 to 30 w % of an ethylenically unsaturated monomer B having as hydrogen bond donor an amide group, said ethylenically unsaturated monomer B being as monomer B1 0.0 to 2 w % of an ethylenically unsaturated monomer having a cyclic amide moiety, and/or as monomer B2 0.0 to 30 w % of an ethylenically unsaturated monomer having an acyclic amide group, with the sum of monomers B1 and B2 being at least 0.1 w %; 30 to 60 w % of at least one ethylenically unsaturated carboxylic acid as monomer C selected from the group consisting of methacrylic acid, acrylic acid and itaconic acid with methacrylic acid making 80 to 100 w % of said monomer C; 0.1 to 10 w % of a macromonomer D; 0 to 0.3 w % of at least one crosslinker E and 0 to 30 w % of at least one further monomer F selected from the group consisting of ethylenically unsaturated cationogenic or cationic monomers and ethylenically unsaturated sulfonic- or phosphonic acids. The sum of the compounds A to F of said copolymer equals 100 w %, the monomer B1 makes from ⅙ to 3.45 times the weight amount of the macromonomer D, and/or the weight amount of the monomer B2 being at least three times higher than the amount of the macromonomer D.

It was shown in a large number of experiments that the copolymers or polymers (where the term polymer and copolymer are alternately used in this text) disclosed in claim 1 are able to meet the requirements as set forth previously.

In particular these polymers provide to a rheological or cosmetic composition when incorporated therein curl retention values of greater than 90%, more preferably equal to or greater than 94% and values of flexural strength being higher than 150 cN, more preferably being higher than 170 cN and most preferably being higher than 190 cN as is exemplarily shown in part three of table 1. Likewise the stiffening effect is good or better as shown in part two of table 1.

In addition to this good performance the compositions comprising the polymers of the invention also show an improved thickening capacity compared to other styling polymers. All of these polymers confer to a cosmetic or rheological composition viscosities above 15.000 mPa, preferably above 18.000 mPA and most preferably above 20.000 mPA as can be seen from part two of table 1 which is only an extract of the compositions tested. This makes a rheological or cosmetic composition comprising the copolymer of the invention more straight forward and cheaper as one can use a smaller or almost no amount of thickening means therein.

Moreover, since one uses only one macromonomer D, the amount of which is small, and the monomer B used is either affordable or employed in low concentrations, the polymers of the invention and their respective compositions in this regard are also cost-effective compared to prior art embodiments.

In order to come to these good performance values, care should be taken when choosing the amount of monomer B and macromonomer D and their respective ratio. Provided that the amount of monomer B and macromonomer D are too high, there is extensive hydrogen bonding in addition to hydrophobic interaction and carboxylic repulsion thus making the rheological or cosmetic preparation too rigid to be handled properly. On the other hand, a too small amount of monomer B and macromonomer D would make handling easier, but one would loose on the styling performance especially on the setting performance of such a composition when used for hair styling. This especially applies if the amount of monomer B is too small. A too small amount of macromonomer D makes the composition of the copolymer more and more heterogeneous which can only be resolved by additional thickener to be added thus making the composition more expensive. However, these drawbacks are not observed with the copolymers of the invention.

The terms "copolymer" or "copolymer of the invention" as well as "polymer" and "polymer of the invention" and their respective plural forms in this text are interchangeable if not expressly indicated otherwise.

If the term "methacrylate" is written in parantheses like "(meth)acrylate", this refers in this whole application text to acrylates and to methacrylates respectively, viz. to esters of methacrylic acids as well as to esters of acrylic acids.

Monomer A, a non-ionic ethylenically unsaturated C1-C4 (meth)acrylate of this invention comprises at least one monomer selected from the group consisting of (C1-C4) alkyl acrylates, (C1-C4) alkyl methacrylates, (C1-C4) hydroxyalkyl acrylates, (C1-C4) hydroxyalkyl methacrylates, vinyl acetate, vinyl propionate, styrene, and alpha-methyl styrene.

In particular for said monomer A at least one representative is selected from the group consisting of n-hydroxybutylacrylate, n-hydroxybutylmethacrylate, 2,3-dihydroxybutylacrylate, 2,3-dihydroxybutylmethacrylate, 2,4-dihydroxybutylacrylate, 2,4-dihydroxybutylmethacrylate, 2,3-dihydroxypropylacrylate, 2,3-dihydroxypropylmethacrylate, hydroxypropylacrylate, hydroxypropylmethacrylate, 2-hydroxyethylacrylate, 2-hydroxyethylmethacrylate, 2-methoxyethylacrylate, 2-methoxyethylmethacrylate, 2-ethoxyethylacrylate, 2-ethoxyethylmethacrylate, methylacrylate, ethylacrylate, propylacrylate, n-butylacrylate, iso-butylacrylate, t-butylacrylate, methylmethacrylate, ethylmethacrylate, propylmethacrylate, n-butylmethacrylate, iso-butylmethacrylate, t-butylmethacrylate.

Among these monomers of monomer A at least one non-ionic ethylenically unsaturated C1-C4 (meth)acrylate being selected from the group consisting of ethylacrylate, tert.-butylacrylate, methylmethacrylate, ethylmethacrylate is highly preferred. It is even further preferred with ethylacrylate making the majority of the monomers of the last sentence. In a highly preferred embodiment monomer A is ethylacrylate or ethylacrylate combined with methylmethacrylate. A mostly preferred embodiment of the invention monomer A consists of ethylacrylate or ethylacrylate combined with methylmethacrylate with ethylacrylate being the only or the predominant component of monomer A.

The concentration of monomer A ranges from 15 to 60 w % and in more detail: The concentration of monomer A comprising two or more monomers ranges from 34.9 to 58.6 w %, preferably from 46 to 57.9 w % and more preferably from 51.8 to 56 w %. The concentration of monomer A comprising one monomer only, ranges from 15 to 56 w %, preferably from 44 to 53 w %, more preferably from 36.7 to 49 w % and in a highly preferred embodiment from 44 to 49 w % of the total weight amount of monomers used. In a mostly preferred embodiment of the invention monomer A comprises between 44 and 49 w % of ethylacrylate. Copolymers of the invention having the mostly preferred quantity of ethylacrylate show the best values as well as regards flexural strength and viscosity.

In another embodiment it was also tested to use as monomer A ethylacrylate in the quantities indicated in the last paragraph and to replace up to 20 w % thereof by at least one non-ionic ethylenically unsaturated C1-C4 (meth)acrylate of the invention. Such embodiments also show the properties of the inventive copolymer; however, not all representatives of this embodiment are tested yet.

The characteristic of the ethylenically unsaturated monomer B is its amide group. Amide group as understood by the invention comprises the following structures:

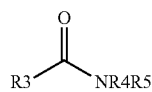 (IV)

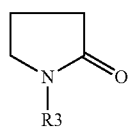 (V)

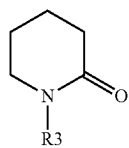 (VI)

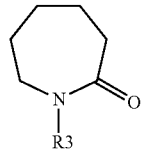 (VII)

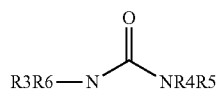 (VIII)

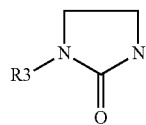 (IX)

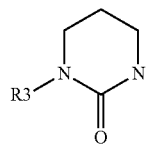 (X)

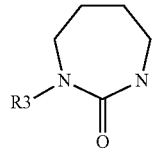 (XI)

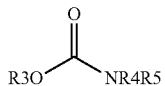 (XII)

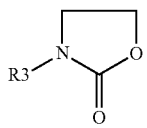 (XIII)

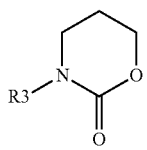 (XIV)

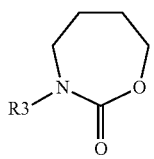 (XV)

wherein R3 is an ethylenically unsaturated moiety $CH_2{=}CH$ or $CH_2{=}C{-}CH_3$ or higher homologues thereof, such that corresponding acrylamides, methacrylamides, N-vinylamides, N-vinylureas and N-vinylurethanes comprising one of the groups acrylic (II), methacrylic (III), maleic, itaconic, crotonic, vinyl and vinylphthalic will be formed (for numerals (II), (III) cf. claim 6). In one embodiment R3 is one such higher homologue viz. methacryloyloxethyl having the following structure with $CH_2$ making the bond:

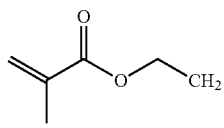 (XVI)

R4 is hydrogen and R5, R6 are radicals selected from hydrogen, methyl, ethyl, n-propyl, isopropyl, n-butyl, isobutyl, tert.-butyl, n-pentyl, isopentyl, cyclopentyl, hexyl and cyclohexyl.

Monomer B is of great importance to the invention due to its amide hydrogen or hydrogen in alpha position to the amide nitrogen, capable of serving as H-bridge donor.

It can be divided into two subclasses viz. monomer B1 and monomer B2.

Monomer B1 comprises a cyclic viz. rigid amide moiety as shown in the formulas (V), (VI), (VII), (IX), (X), (XI), (XIII), (XIV) and (XV).

In a highly preferred embodiment monomer B1 is an ureidomethacrylate having the molecular structure:

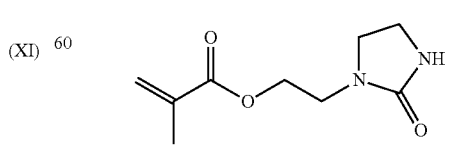 (XVII)

In an alternative embodiment monomer B1 has the molecular structure (XVII) with the imidazolidin-2-one ring being alkylated with a C1-C4 alkyl radical. Said C1-C4 alkyl radical is selected from the group consisting of methyl, ethyl, propyl, isopropyl, n-butyl, isobutyl, tert-butyl with n-butyl being the most preferred one. In the examples representatives of such B1 structures viz. derivatives of (XVII) are termed UR-A or UR-MA.

Said monomer B1 is used either in combination with monomer B2 or as it is or monomer B2 is used instead of it.

In an embodiment the copolymer of the invention comprises 0.1 to 2 w % of the monomer B1, preferably from 0.2 to 2 w %, more preferably 0.3 to 1.5 w % thereof, still more preferably 0.4 to 1 w % thereof and most preferably 0.5 to 1 w %. With these amounts of monomer B1, a composition viz. a rheological or cosmetic composition comprising said copolymer provides very good values for flexural strength and viscosity.

Monomer B2, is any ethylenically unsaturated monomer having an acyclic amide group. In a preferred embodiment monomer B2 is an N-alkyl acrylamide with the N-alkyl group thereof comprising from 2 to 12 carbon atoms, or an N-alkyl methacrylamide with the N-alkyl group thereof comprising from 2 to 12 carbon atoms.

More preferably said monomer B2 is selected from the group consisting of acrylamide, methacrylamide, ethacrylamide, N-methylacrylamide, N,N-dimethylacrylamide with various degrees of N-alkylation, N-ethylacrylamide, N-isopropylacrylamide, N-butylacrylamide, N-tert.-butylacrylamide, N-octylacrylamide, N-tert.-octylacrylamide, N-octadecylacrylamide, N-phenylacrylamide, N-methylmethacrylamide, N-ethylmethacrylamide, N-tert.-butylmethacrylamide, N-dodecylmethacrylamide, N-[3-(dimethylamino)propyl]-methacrylamide with various degrees of alkylation, N-[3-(dimethylamino)propyl]-acrylamide with various degrees of N-alkylation, N-[3-(dimethylamino)-butyl]methacrylamide with various degrees of N-alkylation, N-[3-(dimethylamino)octyl]-methacrylamide with various degrees of N-alkylation, N-[12-(dimethylamino)dodecyl]-methacrylamide with various degrees of N-alkylation, N-[3-(diethyl-amino)propyl]-methacrylamide with various degrees of N-alkylation and N-[3-(diethylamino)propyl]acrylamide also with various degrees of N-alkylation.

Still more preferred said monomer B2 is selected from the group consisting of acrylamide, methacrylamide, ethacrylamide, N-methylacrylamide, N-ethylacrylamide, N-isopropylacrylamide, N-butylacrylamide, N-tert.-butylacrylamide, N-octylacrylamide, N-tert.-octylacrylamide, N-octadecylacrylamide, N-phenylacrylamide, N-methylmethacrylamide, N-ethylmethacrylamide, N-tert.-butylmethacrylamide, N-dodecylmethacrylamide, as these monomers B2 are more easily available.

Even more preferred said monomer B2 is selected from the group consisting of acrylamide, methacrylamide, ethacrylamide, N-methylacrylamide, N-ethylacrylamide, N-methylmethacrylamide, N-ethylmethacrylamide, N-isopropylacrylamide, N-butylacrylamide, N-tert.-butylacrylamide, N-octylacrylamide, N-tert.-octylacrylamide, N-octadecylacrylamide, N-phenylacrylamide and mixtures thereof since these monomers are less bulky.

In a highly preferred embodiment the ethylenically unsaturated monomer B2 is selected from the group consisting of acrylamide, methacrylamide, ethacrylamide, N-isopropylacrylamide, N-butylacrylamide, N-tert.-butylacrylamide, N-octylacrylamide and mixtures thereof.

The most promising candidate for ethylenically unsaturated monomer B2 was shown to be selected from the group consisting of N-tert.-butylacrylamide or methacrylamide or a mixture thereof, since with these affordable monomers B2 one obtains among the highest values for flexural strength and viscosity paired with a good or better stiffening effect when polymers of the invention containing said monomers B2 are part of a cosmetic or rheological composition.

In another embodiment the polymer of the invention is void of monomer B1 and only contains monomer B2, as previously disclosed, which gives an advantage as to the production costs. Furthermore such kind of inventive copolymers show a considerable setting performance.

0 to 30 w %, preferably 0.1 to 30 w % of an ethylenically unsaturated monomer having an acyclic amide group, viz. of monomer B2 are used for the inventive copolymer. More preferably the amount ranges from 0.4 to 20 w % of monomer B2, still more preferably from 0.9 to 15 w %, even more preferred from 4 to 15 w %, still more preferred from 10 to 15 w % and in a highly preferred embodiment from 10 to 14 w % of monomer B2. These concentrations of monomer B2 confer to the polymer of the invention good flexural strength and high viscosity values, viz. good setting and rheology characteristics and the inventive copolymers are affordable due to the competitiveness of monomers B2.

Therefore in an even more preferred embodiment the inventive copolymer comprises from 10 to 14 w % of at least one monomer B2 selected from the group consisting of N-tert.-butylacrylamide and methacrylamide as is or in combination with 0.4 to 1 w %, preferably from 0.5 to 1 w % of monomer B1.

In another preferred embodiment of the invention the sum of the monomers B1 and B2 of the inventive copolymer is at least 0.4 w %, preferably at least 0.5 w %, more preferably at least 1 w %, still more preferred at least 2 w %, further preferred at least 10 w %. In an even further preferred embodiment of the invention the sum of the monomers B1 and B2 ranges from 10 to 14 w %, preferably from 10 to 12 w %, further preferred from 10 to 11 w % and highly preferred from 10 to 10.5 w %. Copolymers of the invention comprising said feature provide rheological or cosmetic compositions with high viscosity and flexural strength values as can be seen from examples 37, 38 and 45.

The inventive copolymer further comprises 30 to 60 w % of at least one ethylenically unsaturated carboxylic acid as monomer C selected from the group consisting of methacrylic acid, acrylic acid and itaconic acid with methacrylic acid making 80 to 100 w % of said monomer C. This amount of ethylenically unsaturated anionic monomers is required in order to solubilize the macromonomer D.

Preferably the ethylenically unsaturated carboxylic acid as monomer C is methacrylic acid.

In another embodiment monomer C is a mixture of methacrylic acid and acrylic acid with methacrylic acid having a concentration which is at least 8 times higher and more preferred 8 times higher than the amount of acrylic acid.

When monomer C exclusively comprises methacrylic acid, its concentration ranges from 30 to 60 w %, preferably from 32 to 50 w %, more preferably from 35 to 45.5 w %, further preferred from 39 to 45 w %, still further preferred from 40 to 43 w %, even more preferably from 40 to 42.5 w %, even further preferred from 40 to 42 w %, still further preferred from 40.125 to 42 w %, even further preferred from 40.125 to 41.6 w %, still further preferred from 40.125 to 41 w %, in an even further advanced embodiment from 40.125 to 40.625 w % and mostly preferred within 40.125 and 40.5 w %.

Provided that monomer C is selected from the group consisting of methacrylic acid and acrylic acid or methacrylic acid and itaconic acid, methacrylic acid is present in concentrations ranging from 0 to 60 w %, preferably from 32 to 60 w %, more preferably from 40 to 55 w %, still more preferably from 40 to 50 w %, even more preferably from 40 to 45 w %, still further preferred from 40.125 to 42 w %, even further preferred from 40.125 to 41.6 w %, still further preferred from 40.125 to 41 w %, in an even further advanced embodiment from 40.125 to 40.625 w % and mostly preferred within 40.125 and 40.5 w % and acrylic acid having a concentration ranging from 0.1 to 15 w %, preferably from 0.9 to 10 w %, more preferably from 2 to 7 w % and most preferably from 2.5 to 5 w %. Replacing methacrylic acid by acrylic acid makes the copolymer of the invention less expensive which provides an economic advantage.

Within these concentration ranges of ethylenically unsaturated carboxylic acid(s) one obtains flexural strength values for a composition of said polymer which are always above 150 cN and in most cases above 170 cN as well as viscosity values thereof being above 18.000 mPa and in many cases even above 20.000 mPa.

However, these ethylenically unsaturated carboxylic acids are far from being the only ones to be adequate for the polymer of the invention. It was shown that acidic vinyl carboxylic acid-containing monomers including, but not limited to ethyl acrylic acid or ethacrylic acid, citraconic acid, maleic acid and its anhydride, fumaric acid, crotonic acid, aconitic acid, and the like as well as C1-C18 alkyl-monoesters of maleic, fumaric, itaconic, or aconitic acid are suitable for being part of the inventive polymer.

Likewise ethylenically unsaturated acids, such as methyl hydrogen maleate, monoisopropyl maleate, butyl hydrogen fumarate, and the like are useful for the inventive polymer. This also applies to anhydrides of dicarboxylic acids, such as maleic anhydride, itaconic anhydride, citraconic anhydride, and the like.

However, mechanical properties' studies with respect to rheological and cosmetic compositions comprising inventive polymers having at least one of these further monomers C of the last two paragraphs are still under way.

The copolymer for rheological or cosmetic compositions comprises as key component 0.1 to 10 w % of a macromonomer D also termed monomer D. This monomer besides its ethylenically unsaturated moiety comprises a polar aprotic mid-section and a hydrophobic end section. Therefore it readily interacts both with highly hydrophobic counterparts and with protic counterparts of the inventive polymer. Thus thickening performance of said polymer is not only achieved by repulsion of carboxylic groups and hydrophobic interaction but also by polar interactions, especially between the oxygen of the polar aprotic mid-section and hydrogen atoms of monomer B.

Furthermore the presence of the macromonomer D contributes to the styling performance of the polymer of the invention in a cosmetic composition.

However, care should be taken as to the concentration of said monomer D. If too much thereof is present in the preparation especially if the concentration of monomer B also is elevated, this would yield a copolymer providing a quite dense rheological or cosmetic composition which is difficult to handle and to portion out. On the other hand, an insufficient amount of said monomer D likewise would hamper the thickening properties of the polymer of the invention in a composition. Further the styling performance is minimized, if the amount of monomer B is reduced too.

Therefore, the copolymer of the invention comprises from 0.1 to 10 w % of the macromonomer D, also termed monomer D. In a preferred embodiment, said concentration ranges from 0.1 to 6 w %, preferably from 0.2 to 4 w %, more preferably from 0.3 to 3 w %, further preferred from 0.375 to 3 w %, in a still further preferred form from 0.375 w % to 2 w %, and still more preferably from 0.3 to 2 w %. Still more preferred the inventive copolymer comprises between 0.375 and 1.6 w % of the macromonomer D and in a still further preferred embodiment 0.375 to 1 w % of said monomer D are used. In a highly preferred embodiment the copolymer comprises between 0.375 w % and 0.75 w % of monomer D and mostly preferred the copolymer comprises from 0.375 w % to 0.5 w % of monomer D.

Depending on the fine-tuned mechanical properties required for the rheological or cosmetic composition the copolymer of the invention introduced therein also requires at least one cross-linker E. Said cross-linker is essential or almost indispensable if the copolymer of the invention is free of monomer B2.

Thus the polymers of the invention can optionally be prepared from a monomer mixture comprising one or more cross-linking monomers E for introducing branching and controlling molecular weight.

One type of cross-linkers E is characterized by their polyunsaturated nature. Monounsaturated compounds carrying a reactive group that is capable of causing a formed copolymer to be cross-linked before, during, or after polymerization has taken place can also be utilized as monomer E. Other useful cross-linking monomers E include polyfunctional monomers containing multiple reactive groups, such as epoxide groups, isocyanate groups, and hydrolysable silane groups.

Examples of suitable polyunsaturated cross-linking monomers E include, without being limited thereto, polyunsaturated aromatic monomers, such as divinylbenzene, divinyl naphthalene, and trivinylbenzene; polyunsaturated alicyclic monomers, such as 1,2,4-trivinylcyclohexane; di-functional esters of phthalic acid, such as diallyl phthalate; polyunsaturated aliphatic monomers, such as dienes, trienes, and tetraenes, including isoprene, butadiene, 1,5-hexadiene, 1,5,9-decatriene, 1,9-decadiene, 1,5-heptadiene; and the like.

Other suitable polyunsaturated cross-linking monomers E include polyalkenyl ethers, such as triallyl pentaerythritol, diallyl pentaerythritol, diallyl sucrose, octaallyl sucrose, and trimethylolpropane diallyl ether; polyunsaturated esters of polyalcohols or polyacids, such as 1,6-hexanediol di(meth)acrylate, tetramethylene tri(meth)acrylate, allyl acrylate, diallylitaconate, diallyl fumarate, diallyl maleate, allylalcohol, trimethylolpropane tri(meth)acrylate, trimethylolpropane di(meth)acrylate, and polyethylene glycol di(meth)acrylate; alkylene bisacrylamides, such as methylene bisacrylamide, propylene bisacrylamide, and the like; hydroxy and carboxy derivatives of methylene bisacrylamide, such as N,N'-bismethylol methylene bisacrylamide; polyethyleneglycol di(meth)acrylates, such as ethyleneglycol di(meth)acrylate, diethyleneglycol di(meth)acrylate, triethyleneglycoldi(meth)acrylate; polyunsaturated silanes, such as dimethyldivinylsilane, methyltrivinylsilane, allyldimethylvinylsilane, diallydimethylsilane and tetravinylsilane; polyunsaturated stannanes, such as tetraallyl tin, diallyldimethyl tin; diallyldimethylammoniumchloride and the like.

Suitable monounsaturated compounds carrying a reactive group include N-methylolacrylamide, N-alkoxy(meth)acrylamide, wherein the alkoxy group is a C1-C18 alkoxy; and unsaturated hydrolysable silanes, such as triethoxyvinylsilane, tris-isopropoxyvinylsilane, 3-triethoxysilylpropyl methacrylate, and the like.

Useful polyfunctional cross-linking monomers containing multiple reactive groups include, but are not limited to hydrolysable silanes, such as ethyltriethoxysilane and ethyltrimethoxysilane; epoxy substituted hydrolysable silanes, such as 2-(3,4-epoxycyclohexyl)ethyltriethoxysilane and 3-glycidoxypropyltrimethyoxysilane; polyisocyanates, such as 1,4-diisocyanatobutane, 1,6-diisocyanatohexane, 1,4-phenylenediisocyanate, and 4,4'-oxybis(phenylisocyanate); unsaturated epoxides, such as glycidylmethacrylate and allylglycidyl ether; and polyepoxides, such as diglycidyl ether, 1,2,5,6-diepoxyhexane and ethyleneglycoldiglycidyl ether; and the like.

Particularly useful are polyunsaturated cross-linkers derived from ethoxylated polyols, such as diols, triols and bis-phenols, ethoxylated with about 2 to about 100 moles of ethylene oxide per mole of hydroxyl functional group and end-capped with a polymerizable unsaturated group, such as a vinyl ether, allyl ether, acrylate ester, methacrylate ester, and the like.

Examples of such cross-linkers include bisphenol A, ethoxylated dimethacrylate; bisphenol F, ethoxylated dimethacrylate, trimethylol propane ethoxylated trimethacrylate, and the like.

Examples of particularly preferred cross-linkers E are allylic ethers of polyols having at least two allylic ether groups. A representative thereof is trimethylolpropane triallylether.

In a highly preferred embodiment the cross-linker E is a compound derived from a tetraol. Said tetraol in a preferred embodiment is a C5-alcohol. In a further preferred embodiment said tetraol which preferentially is a C5-tetraol is connected to ethylenically unsaturated radicals by means of an ether linkage. Mostly preferred the cross-linker E is a C5 tetraol connected via ether linkage to three α,β-ethylenically unsaturated radicals. In the utmost preferred embodiment the cross-linker E is pentaerythritol allyl ether PETAE having the CAS reference number 91648-24-7.

Another suitable crosslinker being structurally related to monomer B1 and being used in examples 19 and 20 in amounts indicated with an asterisk, is diurethane-dimethacrylate (CAS 72869-86-4) sold under the trade name Plex®-6661-O by Evonik.

Cross-linkers having at least two allylic moieties which are connected to the core of the molecule via ether linkages are rather stable during the course of the reaction even in the presence of acids and are readily compatible with several solvent conditions.

For fine tuning the mechanic properties of the polymer of the invention, cross-linkers can also be used in combination. Preferably 0 to 0.3 w % of at least one respective cross-linker are used with PETAE and Plex®-6661-O being the most preferred ones. PETAE was shown to be the most flexible one with regard to reaction conditions and therefore 0 to 0.3 w % thereof are used.

Depending on the target molecule or target composition to be achieved, sometimes cross-linkers can be completely omitted, especially if a combination of N-tert.-butylacrylamide as monomer B2 and macromonomer D are used.

However, otherwise one has the opportunity to use 0.1 to 0.3 w % of a cross-linker, and preferably 0.1 to 0.2 w % thereof. Said cross-linker in a still further preferred embodiment is PETAE.

The copolymer of the invention also comprises between 0 to 30 w % of a further monomer F selected from the group consisting of ethylenically unsaturated cationogenic or cationic monomers and ethylenically unsaturated sulfonic or phosphonic acids. Said compounds are adapted to confer to the polymer of the invention particular properties as for instance still higher solubility in protic or aqueous solvents, or, when incorporated into a cosmetic composition, its capacity to condition a headdress.

Ethylenically unsaturated cationogenic or cationic monomers comprise at least one compound selected from the group consisting of N—(C1-C4)-alkylamino-(C1-C12)-alkyl acrylates, N—(C1-C4)-alkylamino-(C2-C4)-alkyl methacrylates and vinylimidazoles.

Preferably said ethylenically unsaturated cationogenic or cationic monomers are selected from the group consisting of N,N-dimethyl-aminomethyl(meth)acrylate, N,N-diethylaminomethyl(meth)acrylate, N,N-dimethylaminoethyl (meth)acrylate, N,N-diethylaminoethyl-(meth)acrylate, N-butyl-aminoethyl(meth)acrylate, N-tert.-butylaminoethylmethacrylate, N,N-dimethylaminobutyl(meth)acrylate, N,N-diethyl-aminobutyl(meth)acrylate, N,N-dimethylamino-hexyl(meth)acrylate, N,N-dimethylaminooctyl(meth) acrylate, N,N-dimethylaminododecyl-(meth)acrylate, N-vinylimidazole or 1-vinylimidazole, 1-vinyl-2-methylimidazole The ethylenically unsaturated sulfonic acids comprise at least one monomer selected from the group including but not limited to vinyl sulfonic acid, 2-sulfoethyl methacrylate, styrene sulfonic acid, 2-acrylamido-2-methylpropane sulfonic acid (AMPS), allyloxybenzene-sulfonic acid, and the like. Particularly preferred are the sodium salt of styrene sulfonic acid (SSSA) and AMPS.

The ethylenically unsaturated phosphonic acids comprise at least one monomer selected from the group including but not limited to vinyl phosphonic acid, allyl phosphonic acid, 3-acrylamidopropyl phosphonic acid, and the like.

One uses 0 to 30 w %, preferably 0.9 to 15 w % of at least one further monomer F, more preferably ranging from 2 to 15 w % and still highly preferred from 2 to 14 w %.

In a further preferred embodiment the copolymer of the invention comprises as monomer F 2-acrylamido-2-methylpropane sulfonic acid (AMPS) in an amount which is at least 0.1 w % and at most 20 w % of the amount of monomer C used and preferably at least 0.1 w % and at most 15 w % of the amount of monomer C used.

In a highly preferred embodiment the copolymer of the invention comprises 30 to 60 w % of methacrylic acid or 30 to 60 w % of a mixture of monomer C and/or monomer F, said mixture consisting of methacrylic acid and at least one acid selected from the group consisting of acrylic acid, itaconic acid and 2-acrylamido-2-methylpropane sulfonic acid (AMPS).

In an even further preferred embodiment the copolymer of the invention comprises 30 to 60 w % of a mixture of monomer C and/or monomer F, said mixture consisting of methacrylic acid and at least one acid selected from the group consisting of acrylic acid, itaconic acid and 2-acrylamido-2-methylpropane sulfonic acid (AMPS) with said at least one acid making up to 15 w % of the amount of methacrylic acid.

The copolymer of the invention is further characterized in that the monomer B1 makes from ⅙ to 3.45 times, preferably from ⅓ to 2 times, more preferably from 0.4 to 2 times, still more preferably from 0.5 to ⁴⁄₃ time, even more preferably from ⁸⁄₁₅ to ⁴⁄₃ times, still more preferred from ⅔ to ⁴⁄₃ times and most preferably from 1 to ⁴⁄₃ times the weight amount of the macromonomer D. In fact, as already indicated supra, the ratio between ethylenically unsaturated monomer B having as hydrogen bond donor an amide group and macromonomer D is crucial both for the development of the ability of the polymer of the invention to generate in a rheological or cosmetic composition elevated viscosities and at the same time to provide high values of flexural strength. As can be seen from table 1 parts 2 and 3, this is particularly true for examples 37 and 38. Outside these claimed ranges flexural strength values do not come to this high.

A second factor impacting on the ability of the polymer to provide good flexural strength as well as high viscosity values is the weight amount of the monomer B1 being at least 24.95 times, preferably at least 27.45 times, more preferably at least 28.4 times, even more preferably at least 51.9 times, more preferably at least 56.8 times, and most preferably at least 57.8 times smaller than that of the non-ionic monomer A. For the most promising examples it was found that the weight amount of the monomer B1 being at least 98 times smaller, more preferably at least 121.5 times and even more preferably at least 146.5 times smaller than that of the non-ionic monomer A. If the value is beyond the claimed ones this will impair on the performance of a rheological or cosmetical composition with respect to flexural strength and viscosity.

In a highly preferred embodiment the copolymer of the invention comprises 0.2 to 1.5 w % of an ethylenically unsaturated monomer having a cyclic amide moiety as monomer B1, and/or 0.0 to 30 w % of an ethylenically unsaturated monomer having an acyclic amide group, as monomer B2 with the sum of B1 and B2 being at least 0.2.

And most preferably the copolymer of the invention comprises 0.3 to 1 w % of an ethylenically unsaturated monomer having a cyclic amide moiety as monomer B1, and/or 0.0 to 30 w % of an ethylenically unsaturated monomer having an acyclic amide group, as monomer B2 with the sum of B1 and B2 being at least 0.3.

Not only the ratio between monomer B1 and macromonomer D influences on the mechanical properties of the copolymer of the invention, being part of a rheological or cosmetic composition. The same applies to monomer B2, especially when it is the only ethylenically unsaturated monomer B having as hydrogen bond donor an amide group. Therefore, the weight amount of the monomer B2 is at least 6.25 times higher, preferably at least 20/3 times higher, more preferably at least 7.5 times higher, still more preferably at least 28/3 times higher, further preferred at least 10 times higher, still more preferably at least 12.5 times higher, even more preferably at least 40/3 higher, still more preferably at least 50/3 higher, even more preferred at least 56/3 times higher, highly preferred at least 20 times higher and even mostly preferred at least 80/3 higher than the amount of the macromonomer D. One can roughly say the higher the amount of monomer B2 compared to macronomomer D, the higher also the values for flexural strength and viscosity as can be seen in table 1 parts 2 and 3, examples 45 and 48.

In a highly preferred embodiment the copolymer of the invention comprises 0.0 to 2 w % of an ethylenically unsaturated monomer having a cyclic amide moiety, as monomer B1 and 5 to 20 w % of an ethylenically unsaturated monomer having an acyclic amide group as monomer B2, with the sum of B1 and B2 being at least 5.

And most preferably the copolymer of the invention comprises 0.0 to 2 w % of an ethylenically unsaturated monomer having a cyclic amide moiety as monomer B1 and 8 to 15 w % of any other ethylenically unsaturated monomer having an acyclic amide group as monomer B2, with the sum of B1 and B2 being at least 8.

Said monomer B2 as indicated in the two preceding paras. is at least one monomer selected from the group consisting of methacrylamide and N-tert.-butylacrylamide.

A very important component of the inventive polymer is the macromonomer D. It is an ethylenically unsaturated oxyalkylated monomer having the general formula (I):

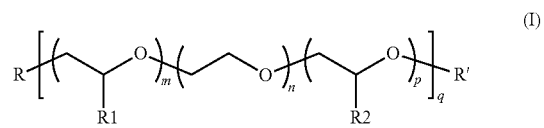

with m and p having a numeral of less than or equal to 50, preferably ranging from 0 to 50, more preferably from 1 to 50, still more preferably from 5 to 30 and most preferably from 10 to 20; n having a numeral ranging from 1 to 50, preferably being less than or equal to 20, more preferably ranging from 1 to 10 and most preferably from 2 to 5; q being a numeral ranging from 1 to 5 and preferably being 1; with the provisio that $(m+n+p) \times q \leq 90$; and R1 representing hydrogen or methyl; R2 being hydrogen or methyl; R being a polymerizable unsaturated moiety selected from the group consisting of

maleic, itaconic, crotonic and vinylphthalic with the oxygen radical thereof making the bond, preferably R being (II) or (III); and R' representing a hydrophobic moiety selected from linear or branched alkyl, alkylaryl or arylalkyl radicals, more preferably from linear alkyl radicals having 8 to 20 carbon atoms, still more preferred from linear alkyl radicals having 12 to 18 carbon atoms and most preferably from linear alkyl radicals having 16 to 18 carbon atoms.

The tripartite structure of this macromonomer D largely influences on the performance of the copolymer of the invention, since it provides (i) means for hydrophilic interaction viz. radical R, (ii) means capable to make hydrogen-bond interaction viz. the polyalkyleneoxy moiety indexed with "q" and (iii) means for hydrophobic interaction, viz. radical R'.

In more detail the portion or means (i) supplying the ethylenically unsaturated end group preferably is derived from an alpha, beta-ethylenically unsaturated mono- or dicarboxylic acid or the anhydride thereof, more preferably a C3 or C4 mono- or dicarboxylic acid or the anhydride thereof. Alternatively, portion (i) of the associative monomer can be derived from an allyl ether or vinyl ether; a nonionic vinyl-substituted urethane monomer, or a vinyl-substituted urea reaction product.

The midsection portion or hydrogen bond interaction means (ii) is preferably a polyoxyalkylene segment of about 5 to about 250, more preferably about 10 to about 120, and most preferably about 15 to about 25 repeating C2-C3 alkylene oxide units: Preferred midsection portions (ii) include polyoxyethylene and polyoxypropylene segments comprising about 5 to about 150, more preferably about 10 to about 100, and most preferably about 15 to about 60 ethylene, or propylene oxide units, and random or non-random sequences of ethylene oxide, and propylene oxide units. In a highly preferred embodiment of the invention hydrogen bond interaction means (II) comprises ethylene oxide units only. Even further preferred q is 1, R1 and R2 are hydrogen, m and p are 10 and n is 5, so that in total 25 ethyleneoxo radicals make the hydrogen bond interaction means (ii).

The hydrophobic interaction means or hydrophobic end group portion (iii) of the macromonomer D is preferably a hydrocarbon moiety belonging to one of the following hydrocarbon classes: a C2-C20 linear alkyl, an aryl-substituted C2-C14 alkyl, a C2-C14 alkyl-substituted phenyl, a C4-C20 branched alkyl, a C5-C20 carbocyclic alkyl.

Preferably, the hydrophobic end groups R' of the macromonomer D are selected from the group consisting of a C2-C20 linear alkyl, a C4-C20 branched alkyl, a C4-C20 carbocyclic alkyl, an aryl-substituted C2-C14 alkyl, a C2-C14 alkyl-substituted phenyl.

Non-limiting examples of suitable hydrophobic groups R' of the hydrophobic interaction means (iii) of the associative monomers are linear or branched alkyl groups having about 8 to about 20 carbon atoms, such as capryl (C8), isooctyl (branched C8), decyl (C10), lauryl (C12), myristyl (C14), cetyl (C16), cetearyl (C16-C18), stearyl (C18), isostearyl (branched C18), arachidyl (C20) and the like.

Further non-limiting examples of linear and branched alkyl moieties having about 8 to 20 carbon atoms that are derived from a natural source include alkyl groups derived from hydrogenated peanut oil, soybean oil and canola oil (all predominantly C18), hydrogenated tallow oil (C16-018), and the like; and hydrogenated C10-C20 terpenols, such as hydrogenated geraniol (branched C10), hydrogenated framesol (branched C15), hydrogenated phytol (branched C20), and the like. Non-limiting examples of suitable C2-C20 alkyl-substituted phenyl groups include octylphenyl, nonylphenyl, decylphenyl, dodecylphenyl, isooctylphenyl, sec-butylphenyl, and the like.

In a particularly preferred embodiment of the macromonomer D, it has as hydrophobic end group R' a C10-C20 linear alkyl group, more preferably a C12-C18 linear alkyl group and highly preferred a C16 to C18 linear alkyl group. In a largely preferred embodiment R' is a cetearyl moiety.

With the means or portions (I), (II) and (III) the macromonomer D is selected from the group consisting of cetyl polyethoxylated (meth)acrylate, cetearyl polyethoxylated (meth)acrylate, stearyl polyethoxylated (meth)acrylate, arachidyl polyethoxylated (meth)acrylate, hydrogenated castor oil polyethoxylated (meth)acrylate, canola oil polyethoxylated (meth)acrylate, where the polyethoxylated portion of the monomer comprises 5 to 40, preferably 10 to 30, and more preferably 20 to 25 ethylene oxide repeating units.

Thus one can use as macromonomer D ceteareth-10 (meth)acrylate, ceteareth-20 (meth)acrylate, ceteareth-25 (meth)acrylate, palmeth-10 (meth)acrylate, palmeth-20 (meth)acrylate, palmeth-25 (meth)acrylate, ceteth-10 (meth)acrylate, ceteth-20 (meth)acrylate, ceteth-25 (meth)acrylate, laureth-25 (meth)acrylate, steareth-10 (meth)acrylate, steareth-20 (meth)acrylate, steareth-25 (meth)acrylate, steareth-10 alkyl ether and steareth-20 alkylether.

In a highly preferred embodiment the macromonomer D of the copolymer of the invention is an ethylenically unsaturated oxyalkylated monomer having the general formula:

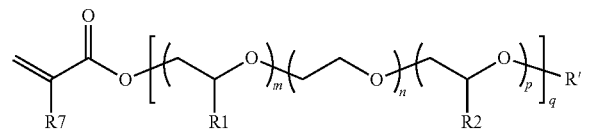

(XVIII)

with
R7 being hydrogen or methyl;
R1 being hydrogen;
m ranging 1 to 50;
n ranging from 4 to 50;
R2 being methyl;
p ranging from 0 to 50;
q being 1
and R' representing a hydrophobic moiety selected from linear alkyl radicals having 8 to 20 carbon atoms.

For this highly preferred embodiment of macromonomer D the preferred concentration ranges of 0.1 to 10 w % as well as 0.1 to 6 w % and so one as indicated supra for all embodiments of macromonomer D apply in the exact same manner.

In a mostly preferred embodiment of the inventive copolymer the macromonomer D is an ethylenically unsaturated oxyalkylated monomer having the general formula (XIX):

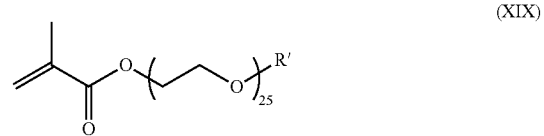

(XIX)

with R' being a linear alkyl radical having 16 to 18 carbon atoms.

Said previously mentioned macromonomer D or monomer D is available under the trade name Plex®-6877-O viz. as $C_{16-18}$-Alkyl $(EO)_{25}$-MA in methylmethacrylate having the weight ratio of 25:75 (CAS 70879-51-5 APG 1100 MA, Evonik). It can also be obtained under the trade name Plex®-6954-O viz. as $C_{16-18}$-Alkyl $(EO)_{25}$-MA in methacrylic acid and $H_2O$ having the weight ratio of 60:20:20 (CAS 70879-51-5 APG 1100 MA, Evonik). Another source is Lutencryl® 250 which stands for $C_{16-18}$-Alkyl $(EO)_{25}$-MA and MAS having a weight ratio of 50:50 (CAS 70879-51-5, (BASF). To be correct Lutencryl® contains 45 w % of methacrylic acid and 5 w % of methylmethacrylate. However, said trace amount of methylmethacrylate cannot be detected in the polymer of the invention for which reason the ratio given is 50 w % monomer D and 50 w % methacrylic acid.

In a preferred inventive embodiment the copolymer of the invention comprises from 0.1 to 10 w % of the macromonomer D, having the general formula (XIX). In a more preferred embodiment, said concentration ranges from 0.1 to 6 w %, preferably from 0.2 to 4 w %, more preferably from 0.3 to 3 w %, further preferred from 0.375 to 3 w %, in a still further preferred form from 0.375 w % to 2 w %, and still more preferably from 0.3 to 2 w %. Still more preferred the inventive copolymer comprises between 0.375 and 1.6 w % of the macromonomer D according to formula (XIX) and in a still further preferred embodiment 0.375 to 1 w % of said monomer D are used. In a highly preferred embodiment the copolymer comprises between 0.375 w % and 0.75 w % of the to formula (XIX) monomer D and mostly preferred the copolymer comprises from 0.375 w % to 0.5 w % of said monomer D of the general formula (XIX).

For high flexural strength values as well as viscosity values obtained with the polymer of the invention in a rheological or cosmetic preparation, a further feature is important, viz. the weight ratio between the macromonomer D combined with monomer B1, or of the macromonomer D as is and the monomer C.

It is required that the weight amount of the sum of monomer B1 and macromonomer D, or of macromonomer D alone is at least 8 times smaller than the weight amount of monomer C used, preferably at least 9 times, more preferably at least 10 times, still more preferred at least 12 times, in an even more preferred embodiment at least 40/3 times, in a further preferred form at least 15 times, more preferably at least 110/7 times smaller, still more preferred at least 17 times smaller, in an further preferred embodiment at least 20 times and more preferred at least 21 times, still further preferred at least 22.5 times, more preferred at least 25 times smaller, highly preferred at least 26 times, even more preferred at least 27 times smaller, further preferred at least 35 times smaller, still further preferred at least 41 times smaller, highly preferred at least 321/7 times smaller, and further highly preferred at least 161/3 times smaller, further at least 163/3 times smaller, still further preferred at least 203/3 times, and in a mostly preferred embodiment at least 81 times smaller, still further preferred at least 90 times smaller, further preferred at least 325/3 smaller, further preferred at least 341/3 smaller and highly preferred at least 365/3 smaller than the weight amount of monomer C used.

If the weight amount of the macromonomer D or the sum of monomer B1 and the macromonomer D is not at least 8 times smaller than the weight amount of monomer C, the copolymer makes a composition thereof more rigid, and thus less easy to handle. Furthermore there is a drawback on the flexural strength values obtained.

Regarding all these data the following embodiments of copolymers were found to have particular suitable properties as regards flexural strength and viscosity.

These polymers were preferentially obtained by emulsion polymerization. Especially if the preparation has more a hydrophobic than a hydrophilic character, emulsion polymerization is mandatory.

A copolymer for rheological or cosmetic compositions comprising
a) 44 to 49 w % of monomer A;
  b1) 0.5 to 1 w % of monomer B1 and/or
  b2) 10 to 14 w % of monomer B2;
  with the sum of monomers B1 and B2 being at least 0.5 w %;
c) 38 to 43 w % preferably 40 to 40.5 w % of monomer C;
d) 0.2 to 1 w % preferably 0.3 to 0.7 w % of the macromonomer D having the formula:

$$\text{(XX)}$$

with
  R8 being hydrogen or methyl;
  z ranging from 15 to 30;
  R' being a linear alkyl radical having 16 to 18 carbon atoms
e) 0 to 0.1 w % of at least one cross-linker E.
  the sum of the compounds A to E equals 100 w %,
with the monomer B1 making from 1/6 to 3.45 times the weight amount of the macromonomer D, and/or
the weight amount of the monomer B2 being at least three times higher than the weight amount of the macromonomer D.

This just mentioned embodiment is particularly suitable for compositions which need to be finely spread and thus have to be highly but not tremendously viscous like styling gels for instance.

A copolymer for rheological or cosmetic compositions comprising
a) 44 to 49 w % of monomer A;
  b1) 0.5 to 1 w % of monomer B1 and/or
  b2) 10 to 14 w % of monomer B2;
  with the sum of monomers B1 and B2 being at least 0.5 w %;
c) 38 to 43 w % preferably 40 to 40.5 w % of monomer C;
d) 0.5 to 4 w % preferably 1 to 3 w % of the macromonomer D having the formula:

$$\text{(XX)}$$

with
  R8 being hydrogen or methyl;
  z ranging from 15 to 30;
  R' being a linear alkyl radical having 16 to 18 carbon atoms
e) 0 to 0.2 w % of at least one cross-linker E.
  the sum of the compounds A to E equals 100 w %,
with the monomer B1 making from 1/6 to 3.45 times the weight amount of the macromonomer D, and/or
the weight amount of the monomer B2 being at least three times higher than the weight amount of the macromonomer D.

This previously mentioned embodiment is particularly suitable for compositions which need to be highly viscous like for instance creams or thickeners for cosmetics, paper preparation or construction materials.

Further preferred embodiments providing high flexural strength viz. a high setting performance and high viscosity values are:

A copolymer comprising
a) 46 to 58.6 w % of ethylacrylate or of a mixture of ethylacrylate and methylmethacrylate;
  b1) 0.1 to 2 w % of monomer B1 and/or;
  b2) 0.4 to 20 w % of monomer B2;
  c1) 40 to 45.5 w % of methacrylic acid or;
  c2) 40 to 55 w % of a mixture of methacrylic acid and acrylic acid with methacrylic acid making 80 to 100 w % of the mixture under c2);
d) 0.375 to 3 w % of a macromonomer D of the formula $$\text{(XIX)}$$

with R' being a linear alkyl radical having 16 to 18 carbon atoms;
  the sum of the compounds A to D equals 100 w %,
with the monomer B1 making from 1/6 to 3.45 times the weight amount of the macromonomer D, and/or
the weight amount of the monomer B2 being at least three times higher than the weight amount of the macromonomer D.

A copolymer comprising
a) 46 to 58.6 w % of ethylacrylate or of a mixture of ethylacrylate and methylmethacrylate;
b1) 0.1 to 2 w % of monomer B1 and/or
b2) 0.4 to 20 w % of monomer B2,
c1) 40 to 45.5 w % of methacrylic acid or
c2) 40 to 55 w % of a mixture of methacrylic acid and acrylic acid with methacrylic acid making 80 to 100 w % of the mixture under c2);
d) 0.375 to 3 w % of a macromonomer D of the formula

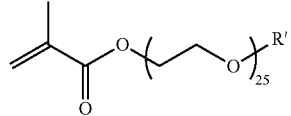

(XIX)

with R' being a linear alkyl radical having 16 to 18 carbon atoms;
e) 0.1 to 0.3 w % of at least one cross-linker E selected from the group consisting of PETAE and Plex®-6661-O,
the sum of the compounds A to E equals 100 w %,
with the monomer B1 making from ⅙ to 3.45 times the weight amount of the macromonomer D, and/or
the weight amount of the monomer B2 being at least three times higher than the weight amount of the macromonomer D.

A copolymer comprising
a) 36.7 preferably 38 more preferably 44 to 49 w % of ethylacrylate;
b1) 0.4 to 1 w % and more preferably 0.5 to 1 w % of monomer B1 and/or;
b2) 4 to 15 w % and more preferably 10 to 14 w % of monomer B2; with the sum of monomers B1 and B2 being at least 0.4 w %;
c1) 40.125 to 40.625 w % and more preferably 40.125 to 40.5 w % of methacrylic acid or;
c2) 40 to 45.625 w % of a mixture of methacrylic acid and acrylic acid with methacrylic acid making 80 to 100 w % of the mixture under c2);
d) 0.375 to 2 w %, preferably 0.375 to 0.5 w % of a macromonomer D of the formula

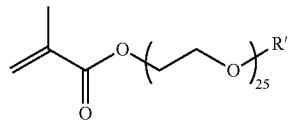

(XIX)

with R' being a linear alkyl radical having 16 to 18 carbon atoms;
the sum of the compounds A to D equals 100 w %,
with the monomer B1 making from ⅙ to 3.45 times the weight amount of the macromonomer D, and/or
the weight amount of the monomer B2 being at least three times higher than the weight amount of the macromonomer D.

A copolymer comprising
a) 36.7 preferably 38 more preferably 44 to 49 w % of ethylacrylate;
b1) 0.4 to 1 w % and more preferably 0.5 to 1 w % of monomer B1 and/or;
b2) 4 to 15 w % and more preferably 10 to 14 w % of monomer B2; with the sum of monomers B1 and B2 being at least 0.4 w %;
c1) 40.125 to 40.625 w % and more preferably 40.125 to 40.5 w % of methacrylic acid or;
c2) 40 to 45.625 w % of a mixture of methacrylic acid and acrylic acid with methacrylic acid making 80 to 100 w % of the mixture under c2;
d) 0.375 to 2 w %, preferably 0.375 to 0.5 w % of an macromonomer D of the formula

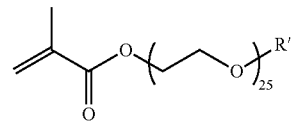

(XIX)

with R' being a linear alkyl radical having 16 to 18 carbon atoms;
e) 0.1 to 0.2 w % of PTAE as cross-linker E;
the sum of the compounds A to E equals 100 w %,
with the monomer B1 making from ⅙ to 3.45 times the weight amount of the macromonomer D, and/or
the weight amount of the monomer B2 being at least three times higher than the weight amount of the macromonomer D.

Furthermore also the copolymers having the following compositions fit well with requirements of the invention viz. to be cost-effective, having high flexural strength and high viscosity values.

A copolymer comprising
a) 44 to 49 w % of monomer A;
    b1) 0.5 to 1 w % of monomer B1 or
    b2) 0.5 to 1 w % of monomer B1 and 10 to 14 w % of monomer B2 or 10 to 14 w % of monomer B2 only;
    with the sum of monomers B1 and B2 being at least 0.5 w %;
c) 40.125 to 45.625 w % preferably 40.125 to 40.5 w % of monomer C;
d) 0.375 to 0.5 w % of the macromonomer D preferably having formula (XiX);
e) 0 to 0.2 w % of at least one cross-linker E.
the sum of the compounds A to E equals 100 w %,
with monomer B1 making from ⅙ to 3.45 times the weight amount of the macromonomer D, and/or
the weight amount of the monomer B2 being at least three times higher than the weight amount of the macromonomer D.

Further preferred is the embodiment previously mentioned with
    a) monomer A being ethylacrylate or a mixture of ethylacrylate and methylmethacrylate;
    b1 the monomer B1 either being absent or being P.-6844-O or being P.-6852-O;
    b2) monomer B2 being N-tert.-butylacrylamide or methacrylamide or a mixture thereof;
    c) monomer C being methacrylic acid or a mixture of methacrylic acid and acrylic acid;
    d) monomer D being monomer XX or P.-6954-O or Lutencryl or P.-6877-O or a mixture of two, three or four of the previously mentioned compounds;
    e) monomer E being absent or PETAE or P.-6661-O or a mixture thereof.

Another aspect of the invention is a rheological or a cosmetic composition comprising as component A the copolymer of the invention, as component B at least one cosmetically or pharmaceutically acceptable carrier chosen from i) water, ii) water-miscible organic solvents, preferably C2-C4-alkanols, in particular ethanol, iii) oils, fats, waxes, iv) esters of C6-C30-monocarboxylic acids with mono-, di- or trihydric alcohols, which are different from iii), v) saturated acyclic and cyclic hydrocarbons, vi) fatty acids, vii) fatty alcohols, viii) propellant gases and mixtures thereof.

The composition further comprises at least one additive different from components A) and B) which is chosen from cosmetically active ingredients, emulsifiers, surfactants, preservatives, perfume oils, thickeners, hair polymers, hair and skin conditioners, graft polymers, water-soluble or dispersible silicone-containing polymers, photoprotective agents, bleaches, gel formers, care agents, colorants, tinting agents, tanning agents, dyes, pigments, bodying agents, humectants, regreasing agents, collagen, protein hydrolyzates, lipids, antioxidants, antifoams, antistats, emollients and softeners.

Typical emulsifiers are anionic surfactants including sodium laurylsulfate, sodium dodecyl benzene sulfonate, sodium dioctyl sulfosuccinate, sodium di-sec-butyl naphthalene sulfonate, disodium dodecyl diphenyl ethersulfonate, disodium laureth-3 sulfosuccinate, disodium n-octadecyl sulfosuccinate, phosphate esters of branched alcohol ethoxylates, and the like.

Typical compositions are in the form of a liquid, gel, foam, spray, mousse, spritz, ointment, cream, emulsion, suspension, lotion, milk, solid or semisolid or paste Due to the performance of the polymer of the invention, rheological and cosmetic compositions are obtained which meet the requirements as described in the object of the invention. Especially compositions comprising said inventive polymer show high viscosity values viz. a good thickening capacity and a high flexural strength the later one being a prerequisite for a good styling polymer.

This can be clearly seen from FIG. 1 disclosing the flexural strength in cN of different hair styling compositions comprising a styling polymer and 0.5 w % of Carbopol® 980 as thickener. Carbopol® 980 is a carbomer viz. a homopolymer of acrylic acid crosslinked with an allyl ether of pentaerythritol, an allyl ether of sucrose, or an allyl ether of propylene having the INCI Monograph ID: 5092 and the CAS No: 9003-01-4. Said mentioned compositions were made as indicated infra under "Preparation of a gel" and the flexural strength was determined as indicated under "Determination of the flexural strength Bt . . . ".

One observers a composition comprising the inventive copolymer to give a flexural strength Bt of greater than 190 cN. In comparative examples hair styling compositions were prepared as indicated in the last para., however with other styling copolymers like Luviskol K90, or Luviset Clear, or Polyacrylate-2-Crosspolymer, or Polyacrylate-14 or VP/Dimethylaminoethylmethacrylate Copolymer instead of the inventive copolymer.

All these other styling copolymers can be used in cosmetic compositions as hair fixative polymers i.e. as hair styling and hair setting polymers.

For instance, Luviskol® K90 (CAS No: 9003-39-8) having the INCI-name PVP is a linear polymer that consists of 1-vinyl-2-pyrrolidone monomers and according to the INCI-database can be used as a binder, emulsion stabilizer, film former, suspending agent, nonsurfactant and as a hair fixative. Said copolymer when part of the cosmetic composition like the inventive copolymer only shows a flexural strength bt of about 61 cN.

Luviset Clear®, (CAS No: 38139-93-4) having the INCI-name VP/Methacrylamide/Vinyl Imidazole Copolymer, is reported to be a film former and a hair fixative. In that same previously indicated cosmetic composition it provides a flexural strength bt of only 91 cN.

Polyacrylate-2-crosspolymer (INCI Monograph ID: 21338), commercialized under the trade name Fixate™ Superhold according to INCI is a copolymer of PEG/PPG-23/6, Dimethicone citraconate, C10-30 alkyl PEG-25 methacrylate, and one or more monomers of acrylic acid, methacrylic acid or one of their simple esters, crosslinked with trimethylolpropane PEG-15 triacrylate. Reported functions of this copolymer are film former and hair fixative. In the prepared cosmetic composition said copolymer only gives a flexural strength bt of 147 cN.

Polyacrylate-14, having the INCI Monograph ID: 18903, sold under the trade name Fixate™ PLUS Polymer, is a copolymer of PEG-25 C10-30 alkyl ether methacrylate, PEG/PPG-5/5 alkyl ether and one or more monomers consisting of acrylic acid, methacrylic acid or one of their simple esters. This copolymer is reported to be a film former and shows in the above indicated cosmetic composition a flexural strength bt of only 67 cN.

Finally VP/Dimethylaminoethylmethacrylate Copolymer, (CAS No: 30581-59-0), sold under the tradenames Copolymer 845™, Copolymer 937™ and Copolymer 958™, is a polymer prepared from vinylpyrrolidone and dimethylaminoethylmethacrylate monomers. According to INCI it servers as a binder, film former, suspending agent, nonsurfactant and as a hair fixative. When it is incorporated into a cosmetic composition as indicated previously, it only provides a flexural strength bt of 70 cN.

One realizes that the inventive copolymers provide a styling or setting performance which is roughly 30 to 120% higher compared to the comparative copolymers in FIG. 1.

Furthermore the comparative styling copolymers in FIG. 1 are not referred in the INCI data base to be a viscosity increasing agent. They just serve the purposes indicated supra. In contrast the polymers of the invention when incorporated into cosmetic compositions also show thickening behaviour and thus increase the viscosity of a composition and consequently modify its rheology. Thus economizing thickener makes the composition of the invention cheap.

This can be seen from Table 3 below disclosing blends containing a styling copolymer and 0.5 w % of Carbopol® Ultrez 21 as thickener, which is a copolymer of C10-C30 alkyl acrylate and one or more monomers of acrylic acid, methacrylic acid or one of their simple esters crosslinked with an allyl ether of sucrose or an allyl ether of pentaerythritol referred under INCI Monograph ID 4663 as Acrylates/C10-30 Alkyl Acrylate Crosspolymer.

TABLE 3

| Profile Properties | 1% Luviskol K90 BASF 0.5% Ultrez 21 | 1% Luviset Clear BASF 0.5% Ultrez 21 | 1% Luviskol VA64W* BASF 0.5% Ultrez 21 | 1% Luviquat Supreme BASF 0.5% Ultrez 21 | 2.5% Luviset Clear 0.5% Inventive Cop 0.5% Ultrez 21 | 2.0% Luviset Clear 1.0% Inventive Cop 0.5% Ultrez 21 |
|---|---|---|---|---|---|---|
| Viscosity [mPa] at pH | 16.400 at pH 6.9 | 12.800 at pH 6.8 | 9.800 at pH 6.8 | 11.800 at pH 6.9 | 21.100 at pH 6.9 | 24.050 at pH 7.1 |
| Clarity (subjective and Transmission [%]) | turbid 40% | turbid 83% | turbid 36% | turbid 3% | almost clear 96% | almost clear 94% |

TABLE 3-continued

| Profile Properties | 1% Luviskol K90 BASF 0.5% Ultrez 21 | 1% Luviset Clear BASF 0.5% Ultrez 21 | 1% Luviskol VA64W* BASF 0.5% Ultrez 21 | 1% Luviquat Supreme BASF 0.5% Ultrez 21 | 2.5% Luviset Clear 0.5% Inventive Cop 0.5% Ultrez 21 | 2.0% Luviset Clear 1.0% Inventive Cop 0.5% Ultrez 21 |
|---|---|---|---|---|---|---|
| Flexural strength; [cN ] rating subjective; 1 is best) | | | | | 228 ± 10 2 | 246 ± 13 2 |
| Curl retention (90% rel. H.; 25° C.); [%] | | | | | 96 | 96 |
| Structure of gel 1 = smooth; 3 = coarse | 1 | 1 | 1 | 1 | 2 | 2 |

Compositions comprising no inventive copolymer show viscosity values far below 20.000 mPa whereas compositions containing said inventive copolymer (termed "Inventive Cop" in table 3) show viscosities above 20.000 mPa. Furthermore these viscosities increase with increasing amounts of inventive copolymer and decreasing amounts of styling polymer.

Table 3 also indicates that despite its capacity to also work as a viscosity increasing agent, the copolymers of the invention do not loose their ability to provide a good setting for hair dos. Flexural strength values (equivalent to flexural strength Bt values) were observed to be with 228 cN and 246 cN even higher with the carbomer Carbopol® Ultrez 21 than with the carbomer Carbopol® 980 as shown in FIG. 1.

Another advantage resulting from the use of inventive copolymers in cosmetic especially hair cosmetic compositions is its ability to make said compositions clearer, which cannot be obtained with compositions only containing a styling copolymer and a carbomer or a carbomer type thickener. Therefore compatibility of viscosity increasing agents and styling or setting copolymers can be improved by means of the inventive copolymers.

The invention also comprises a process for preparing a copolymer of the invention comprising the steps a) preparing an aqueous solution containing between 2 and 10 w % of a mixture containing the monomers of the copolymer of the invention under stirring; b) heating up to a temperature ranging from 30° C. to 60° C. under nitrogen with stirring; c) adding an aliquot of at least one polymerization initiator with stirring and heating up to a reaction temperature ranging from 70° C. to 100° C.; d) supplementing the reaction with the remainder of the mixture of step a) during a time ranging from 0.5 to 4 hours; e) adding the residual polymerization initiator of step c during the course of step d); f) thereafter maintaining the reaction at the reaction temperature for another 0.5 to 2 hours and then cooling it down to 40° C. to 60° C.; g) and adding a mixture of an oxidizing agent and a radical scavenger for a time ranging from 15 min to 2 hours.

Preparing polymers that way is straight forward, cost-effective and gives polymers of the invention in high yields.

However, said process for some monomer combinations requires much time to be conducted due to the different capacity of the various monomers of said monomer combinations to be timely solubilized. Therefore the inventive process for these various monomers comprises the step a of solubilizing all monomers of the invention having a solid state in a liquid monomer or monomer mixture or in a solvent being soluble in water prior to realizing steps a) to g) of the inventive process.

Preferably the polymers of the invention are obtained by emulsion polymerization. This rather cost-saving process gives high yields and the polymers obtained can be used as is, viz. also together with the emulsifier used for preparing a cosmetic or a rheological composition. Especially if the preparation has more a hydrophobic than a hydrophilic character, emulsion polymerization is mandatory.

In a further preferred embodiment, copolymers of the invention or compositions thereof are neutralized. For this at the earliest after step e) of process claim 13, the aqueous solution is neutralized by means of a water-soluble base. In a highly preferred embodiment said water-soluble base is a member selected from the group consisting of ammonia water, lithium hydroxide, potassium hydroxide, sodium hydroxide, monoethanolamine, diethanolamine, triethanolamine, monopropanolamine, dipropanolamine, tripropanolamine, morpholine, aminoethylethanolamine, aminomethylpropanol like 2-amino-2-methyl-1-propanol, aminomethylpropanediol, hydroxyethyl morpholine, ammonium salts of lysine, ammonium salts of glycine and mixtures thereof.

Protection is also sought for using the copolymer of the invention for improving the setting- and hold performance of cosmetic compositions comprising solutions, emulsions, dispersions, pastes and gels applied to a hair do.

In particular the copolymer of the invention is used for improving the setting- and hold performance of cosmetic compositions comprising a combination of a hair styling gel and at least one carbomer- or carbomer-type thickener applied to a hair do. Carbomer is a homopolymer of acrylic acid crosslinked with an allyl ether of pentaerythritol, an allyl ether of sucrose, or an allyl ether of propylene and is registered under the INCI monograph ID: 5092. It covers the compounds listed under CAS No: 9003-01-4, 9007-16-3, 9007-17-4, 9062-04-8 and 76050-42-5 and also includes homopolymers of acrylic acid. Carbomer type thickeners are compounds comprising acrylic acid cross-linked with other allyl ethers as mentioned before.

In particular the copolymer of the invention is used for improving the setting- and hold performance of cosmetic compositions comprising a combination of a hair styling gel and Carbopol® 980 (CAS No: 9003-01-4) as carbomer- or carbomer-type thickener applied to a hair do.

Besides its styling and setting qualities the copolymers of the invention also modify the texture of a cosmetic composition. Therefore protection is also sought for using the copolymer of the invention for modifying the rheology especially the thickening capacity in a preparation including a solution, emulsion, dispersion, paste, gel and the like, especially in a highly salt-loaded preparation.

Since modification of styling and rheological properties of a cosmetic composition are both addressed by the copolymer of the invention, protection is also requested for simultaneously modifying the rheology especially the thickening capacity in a preparation including a solution, emulsion, dispersion, paste, gel and the like, especially in a highly salt-loaded preparation, and improving the setting- and hold performance of a cosmetic especially hair cosmetic composition. Most preferably the preparation and the cosmetic composition are one and the same embodiment.

The uses of the inventive polymer as hair styling respectively hair setting means and as rheology modifying means have a considerable impact on the consumption of raw matter, especially on additional thickeners for rheology modifying compositions of the invention. Said consumption is remarkably reduced since the copolymer of the invention, in its composition performs itself already like a thickener. However, at the same time, increasing thickening capacity does not work against the hair setting performance of such inventive polymer. To the contrary, said polymer of the invention has a good setting capacity when incorporated into a cosmetic composition in addition to its thickening property.

The synthesis of one polymer of the invention is shown exemplarily hereafter: Said process is to be applied for other embodiments of the invention with respectively adapted concentrations.

For this example and for the following ones these abbreviations apply:
EA Ethylacrylate
EMA Ethylmethacrylate
MMA Methylmethacrylate
TBA tert.-Butylacrylate
NTBAM N-tert.-Butylacrylamide
MAM Methacrylamide
AS Acrylic Acid
MA Methacrylate
MAS Methacrylic Acid
AMPS 2-Acrylamido-2-methyl-1-propansulfonic Acid
P.-6877-O=Plex®-6877-O stands for $C_{16-18}$-Alkyl $(EO)_{25}$-MA and MMA in the weight ratio of [25:75] (CAS 70879-51-5 APG 1100 MA, Evonik)
P.-6954-O=Plex-6954®-O stands for $C_{16-18}$-Alkyl $(EO)_{25}$-MA, MAS and $H_2O$ in the weight ratio of [60/20/20] (CAS 70879-51-5 APG 1100 MA, Evonik)
Lutencryl=Lutencryl® 250 stands for $C_{16-18}$-Alkyl $(EO)_{25}$-MA and MAS in the weight ratio of [50:50] (CAS 70879-51-5, (BASF)
P.-6852-O=Plex®-6852-O stands for N-(2-Methacryloyloxyethyl)-ethylene urea (also referred to as ureidomethacrylate or UMA belonging to the group of monomer B1) and $H_2O$ in the weight ratio of [50:50] (CAS 86261-90-7, Evonik)
P.-6844-O=Plex®-6844-O stands for N-(2-Methacryloyloxyethyl)-ethylene urea (also referred to as ureidomethacrylate or UMA belonging to the group of monomer B1) and MMA in the weight ratio of [25:75] (CAS 86261-90-7, Evonik)
UR-A N-(2-Acryloyloxyethyl)-ethylene urea alkylated with a C4-chain (also referred to as C4-urethane-ethylene-acrylate, (BASF), said monomer is an ureidomethacrylate belonging to the group of monomer B1
UR-MA N-(2-Methacryloyloxyethyl)-ethylene urea alkylated with a C4-chain (also referred to as C4-urethane-ethylene-methacrylate, (BASF), said monomer is an ureidomethacrylate belonging to the group of mono mer B1
P.-6661-O=Plex®-6661-O stands for Diurethane-dimethacrylate (CAS 72869-86-4, (Evonik)
PETAE Pentaerythritoltriallylether (CAS 91648-24-7)
P.-6852-O, P.-6844-O, UR-A and UR-MA are abbreviated UMA-M in the headline of table 1 part 1 and UMA-M stands for monomer B1.

Composition of the copolymer synthesized:

| Monomer | Amount in w % |
|---|---|
| EA | 43.97 |
| NTBAM | 5 |
| MAS | 40 (41.2) |
| AS | 5 |
| P.-6954-O | 6 [4.8] (3.6) |
| PETAE | 0.03 |

Note:
The first value for P.-6954 O shown in the table above indicates the amount of Plex ®-6954 used, whereas the second numeral in brackets gives the amount of polymerizable monomers within said value and the third numeral in parentheses indicates the amount of macromonomer D within said value.

| Raw Mixture | |
|---|---|
| Water | 500 g |
| Sodium laureth sulfate | 0.3 g |
| From Feed 2 | 35 g |
| Feed 1 | |
| Sodium peroxodisulfate | 3.5 g |
| Feed 2 | |
| Water | 166 g |
| Sodium laureth sulfate | 2.5 g |
| Tween ® 80 (from plant origin) | 12.0 g |
| EA | 175.9 g |
| MAS | 160.0 g |
| AS | 20.0 g |
| NTBAM | 22.0 g |
| P.-6954-O | 24.0 g |
| PETAE | 0.17 g |
| Feed 3 | |
| Hydrogenperoxide (3 w %) | 22.0 g |
| Feed 4 | |
| Ascorbic Acid | 33 g |

Tween ® 80 (= polyoxyethylene (20) sorbitan monooleate) is solubilized in EA and supplemented with sodium laureth sulfate and water with stirring.
NTBAM, P.-6954-O and PETAE are solubilized in the mixture of MAS and AS. The two phases are combined with stirring.

The raw mixture is heated to 40° C. with stirring under nitrogen, supplemented with an aliquot of feed 1, heated to 80° C., supplemented with feed 2 with stirring for 2 h and after 1 h the second part of feed 1 is added. The mixture is reacted for 1 further hour and then cooled to 60° C.

Thereafter feed 3 is added and feed 4 is added for one hour under stirring after which the sample is cooled and filtered off.

In order to show the different properties of copolymers of the invention and the behavior of their respective gels, several copolymers were prepared as shown in table 1 and introduced in a hair styling composition.

Table 1 part 1 below shows the weight amount of the different monomers used in several examples.

TABLE 1 part 1

| No. | 1.(Meth) Acrylat | (Meth) Acrylamid | MAS | AS | $C_{16-18}$-(EO)-MA M.-Mixture | UMA- M.-Mixture | PETAE P.-6661-OO |
|---|---|---|---|---|---|---|---|
| 02 | EA 47.93 | MMA (9) | — | 40 | — P.-6877-O 8 (2) | P.-6844-O 4 (1) | 0.07 |
| 20 | EA 45.8 | MMA (6) | NTBAM-12 | 30 (32) | — 6877-O 8 (2) Lutencryl 4 (2) | — | 0.2 *) |
| 32 | EA 44 | | NTBAM 14 | 40 (40.5) | — P.-6954-O tq 2.5 [=2] (1.5) | — | — |
| 33 | EA 45 | | NTBAM 14 | 40 (40.25) | — P.-6954-O tq 1.25 [=1](0.75) | — | — |
| 37 | EA 49 | | NTBAM 10 | 40 (40.125) | — P.-6954-O tq 0.625[=0.5] (0.375) | P.-6852-O tq 1 (=0.5) | — |
| 38 | EA 49 | | MAM 10 | 40 (40.125) | — P.-6954-O tq 0.625[=0.5] (0.375) | P.-6852-O tq 1 (=0.5) | — |
| 40 | EA 49 | | NTBAM 10 | 40 (40.25) | — P.-6954-O tq 1.25 [=1] (0.75) | — | — |
| 42 | EA 49 | | NTBAM 10 | 40 (40.5) | — Lutencryl 1.0 (0.5) | — | — |
| 43 | EA 49 | | NTBAM 10 | 40.25 (40.625) | — Lutencryl 0.75 (0.375) | — | — |
| 44 | EA 49 | | NTBAM 10 | 35.25 (35.625) | 5 Lutencryl 0.75 (0.375) | — | — |
| 45 | EA 44 | | NTBAM 10 | 40.25 (40.625) | 5 Lutencryl 0.75 (0.375) | — | — |
| 46 | EA 47 | | NTBAM 10 | 40.25 (40.625) | 2 Lutencryl 0.75 (0.375) | — | — |
| 48 | EA 49 | | MAM 10 | 40 (40.5) | — Lutencryl 1 (0.5) | — | — |
| 49 | EA 48.8 | | MAM 10 | 40 (40.6) | — Lutencryl 1.2 (0.6) | — | — |
| 50 | EA 48.5 | | MAM 10 | 40 (40.75) | — Lutencryl 1.5 (0.75) | — | — |
| 61 | EA 46 | | NTBAM 10 | 40 (41) | — P.-6954-O tq 5 [=4] (3) | — | — |
| 62 | EA 45.97 | | NTBAM 10 | 40 (41) | — P.-6954-O tq 5 [=4] (3) | — | 0.03 |

Table 1 part 2 gives certain values obtained with compositions of the copolymers cited in table 1 part 1.

part 2

| Exp.-No | Polymer w.-% | Thickener, Setting Agent | Thickener, Setting Agent w-% | Appearance | Viscosity mPa | pH | Stiffening Effect |
|---|---|---|---|---|---|---|---|
| 02 | 1.5 | Ultrez 21 | 0.3 | clear | 29.000 | 7.6 | weak |
| 20 | 2.0 | Ultrez 21 | 0.5 | clear | 29.200 | 7.2 | — |
| 32 | 2.0 | Carbopol ® 980 | 0.5 | clear | 34.800 | 6.8 | good |
| 33 | 2.0 | Cabopol ® 980 | 0.5 | clear | 19.600 | 6.9 | good |
| 37 | 2.0 | Carbopol ® 980 | 0.5 | clear | 27.250 | 6.8 | very good |
| 38 | 2.0 | Carbopol ® 980 | 0.5 | clear | 28.050 | 7.1 | good |
| 40 | 2.0 | Carbopol ® 980 | 0.5 | clouded | 23.100 | 6.8 | good plus |
| 42 | 2.0 | Carbopol ® 980 | 0.5 | clouded | 21.300 | 6.8 | good. |
| 43 | 2.0 | Carbopol ® 980 | 0.5 | almost clear | 19.450 | 7.0 | still good |
| 44 | 2.0 | Carbopol ® 980 | 0.5 | almost clear | 25.400 | 7.1 | good. |
| 45 | 2.0 | Carbopol ® 980 | 0.5 | almost clear | 31.350 | 6.9 | good. |
| 46 | 2.0 | Carbopol ® 980 | 0.5 | almost clear | 28.700 | 7.0 | good. |
| 48 | 2.0 | Carbopol ® 980 | 0.5 | almost clear | 21.800 | 7.0 | good. |
| 49 | 2.0 | Carbopol ® 980 | 0.5 | almost clear | 28.800 | 6.9 | good. |
| 50 | 2.0 | Carbopol ® 980 | 0.5 | clear | 36.900 | 7.0 | good. |
| 61 | 2.0 | Carbopol ® 980 | 0.5 | clear | 43.200 | 7.0 | good. |
| 62 | 1.0 | Carbopol ® 980 | 0.5 | clouded | 37.800 | 7.1 | good. |

Table 1 part 3 indicates further mechanical data obtained with compositions of copolymers of table 1 part 1.

part 3

| Exp.-No | Washability | Stickiness Kempf 20° C., 80% r. H.t | Sensory Stickiness | Transmission at 600 nm | Flexural strength Bt [cN] | C.R. [%] |
|---|---|---|---|---|---|---|
| 02 | good | 0-1 | 1 | — | 16 | 37 |
| 20 | | — | — | — | — | — |
| 32 | good | 2-3 | 3 | — | 177 ± 7 | — |
| 33 | good | 2-3 | 3 | — | 189 ± 8 | — |
| 37 | good | 2-3 | 2 | — | 264 ± 6 | — |
| 38 | good | 2 | 2-3 | 97% | 199 ± 10 | 97 |
| 40 | still good | 2-3 | 2-3 | 92% | 175 ± 10 | 97 |
| 42 | still good | 2 | 2 | — | 151 ± 13 | 96 |
| 43 | good | 2-3 | 2 | 92% | 154 ± 13 | 95 |
| 44 | good | 2 | 2 | 94% | 171 ± 11 | 96 |
| 45 | good | 2 | 2 | 94% | 206 ± 6 | 98 |
| 46 | good | 2-3 | 2 | 93% | 188 ± 8 | 96 |
| 48 | good | 2 | 3 | 92% | 196 ± 2 | 94 |
| 49 | good | 2 | 2 | 93% | 191 ± 7 | 96 |
| 50 | good | 2 | 2 | 95% | 195 ± 7 | 93 |

TABLE 1-continued

| 61 | good. | — | — | — | 231 | — |
| 62 | good. | 0-1 | 1 | — | 126 | 98 |

Values without parentheses indicate the amount of metered monomer whereas values in parentheses show the real amount of each monomer used.
The first value for P.-6954 O shown in the table 1 indicates the amount of Plex ®-6954 used, whereas the second numeral in brackets gives the amount of polymerizable monomers within said value and the third numeral in parentheses indicates the amount of macromonomer D within said value.

One recognizes that all compositions comprising Carbopol® 980 and a polymer of the invention provide high values of flexural strength and viscosity. They also show a good stiffening effect as well as good washability properties.

Methods for determining the different mechanical properties of the compositions comprising different polymers of the invention.

Preparation of a gel, viz. one composition of the copolymers of the invention (the amounts have to be adjusted as indicated in table 1 part 2):

An aqueous solution containing 1 w % of Carbopol® 980 or Carbopol® Ultrez 21 (CAS No. 9003-01-4 acrylic acid polymer) was prepared.

An aqueous (if required neutralized) solution containing 6 w % of dried copolymer of the invention was prepared now referred to as copolymer solution.

The respective amount of the copolymer solution was than added to said Carbopol® 980 solution by means of a dropping funnel for a period of 30 min with constant stirring and further stirring for at least another 30 min. The gel thus formed containing 0.5 w % of Carbopol® 980 or Carbopol® Ultrez 21 was centrifuged and evaluated after 24 h.

Appearance:

Appearance is to be monitored by at least two persons. They determine the appearance of the rheological or cosmetic composition further its homogeneity and its colour. Appearance is determined to be clear, almost clear, clouded or turbid.

Determination of the viscosity of compositions of the invention:

The viscosity of the composition of the invention was measured at room temperature in mPa s by means of a Brookfield RVT viscosimeter into which the gel as indicated supra was injected.

Determination of the pH

The pH of the rheological or cosmetic composition comprising a polymer of the invention was determined by means of a glass electrode for instance from Knick Elektronische Meßgeräte GmbH & Co. KG, Berlin Germany.

Homogeneity

The homogeneity was determined by at least two persons and evaluated on a scale from 1 to 4 with:
1=very homogenous film, no inclusions
2=homogenous film with very small irregularities
3=homogeneous film showing already some aberrations
4=irregular structure almost no continuous film Determination of the stiffening effect of a hair styling composition treated—viz. a gel-treated hair strand:

Preparation of a gel for hair styling purposes comprising the copolymer of the invention was realized as indicated under "Preparation of a Gel . . . ".

1 g of said gel was applied onto a hair strand having a length of approximately 23 cm by means of a spatula and spread in the hair strand's direction with the fingers. Said strand dried over night at room temperature and was analyzed by at least two persons the next day. The results obtained are ranged as follows:

| very good | very good stiffening effect |
| good + | more than good stiffening effect |
| good | good stiffening effect |
| still good | still good stiffening effect |
| weak | poor stiffening effect |

Washability

A hair strand treated with the composition of the invention is washed in a 37° C. solution containing Texapon-NSO (CAS 68891-38-3) by soaking it and squeezing it for 15 sec. This is repeated five times. Thereafter the strand is rinsed for 15 sec. with tab water. This soaking, squeezing and rinsing is once repeated. The strand is then squeezed onto filter paper and dried over night. The washability will be determined the next day from at least two persons. Parameters evaluated are the strands ability to be combed, its tendency to stick, its sensation when grasped and the quantity of composition residues The results obtained are:

| very good | all paramteres are excellent |
| good | at least three of the four paramters are excellent |
| still good | two of the parameters are excellent |
| not good | does not meet the previously mentioned cirteria |

Stickiness according to Kempf of a hair styling composition of the invention:

The composition to be analyzed, viz. the composition comprising a copolymer of the invention and prepared as indicated supra was applied as a thin layer onto a glass plate. Once the layer dried to form a film, the film supplemented glass plate was stored over night at 20° C. and 80% of relative humidity in a climatic cabinet. Said plate was then placed onto a Kempf apparatus. 5 mm above the film obtained from the gel a tape was mounted to the apparatus, said tape being a plastic-carbon tape of Pelikan 2060 type having a width of 50 mm. By means of a round rubber stamp (diameter 400 mm, hardness according to Shore A of 60±5) said tape was pressed onto the film for 10 sec. with a force of 250±5 N. The more the film surface is sticky the more particles of the plastic-carbon tape will remain on the film.

The evaluation ranges from 0 to 5 such that the respective values are to be understood as follows:

| 5 | extremely sticky |
| 4 | very sticky |
| 3 | sticky |
| 2 | less sticky |
| 1 | hardly sticky |
| 0 | not sticky at all |

Measurement of the sensory stickiness of a hair strand treated with a hair styling composition of the invention:

Said stickiness was determined with moistened hands. 1 g of the composition of the invention as shown supra in "Preparation of a gel . . . " was applied onto each side of a hair strand and combed into said strand which has a width of 6 cm and a length of 23 cm (thus 2 g of gel in total were applied). The strand was dried for at least 3 h after which the stickiness thereof was determined by at least two persons. They moistened their hands by means of a wet window cloth for 10 sec. after which they compressed the hair strand in the hand for 10 sec. Upon releasing said strand from the hands the sensory stickiness was evaluated. For means of comparison at least one standardized gel was used.

Evaluation is made in a range from 0 to 3 as follows:

| 0 | not at all sticky |
|---|---|
| 1 | hardly sticky |
| 2 | sticky |
| 3 | extremely sticky |

Transmission

The composition of the invention was placed into cuvettes made of quartz and transmission was recorded with a spectrophotometer at 600 nm with water being in the reference cuvette.

Determination of the flexural strength Bt of a hair strand treated with a hair styling composition of the invention:

A composition of the copolymer of the invention as indicated supra was prepared as hair styling composition. 50 g of said gel were dissolved in deionized water to get a solution of 220 ml. A dried hair strand having a length of 24 cm was weighed. 3 g thereof were immersed in the solution previously prepared, removed thereof and excess solution was stripped. Immersing, removing and stripping was realized three times in order to achieve a homogeneous reparation of the solution in the hair strand.

The last stripping of excess solution was done with thumb and forefinger. Further removal of the solution was realized by pressing the hair strand between filter paper such that the hair strand's weight increases by 1 to 1.4 g (with regard to the initial weight of the hair stand). The strand thus obtained was arranged in order to have a round cross-section and was stored at 20° C. and 65% of relative humidity over night in a climatic chamber.

Analysis of the strand prepared was realized in the climatic chamber having the climatic conditions mentioned before by means of a pull and compression analyzer (Easytest 86 8002, Fa. Frank). The hair strand was placed in a symmetrical way on two cylindrical rolls of the sample holder, said rolls having a diameter of 4 mm and being separated from each other by a distance of 9 cm). By means of a rounded stamp approached from the upper side of the strand and in the exact middle thereof the strand was bent by 40 mm which leads to fracture the gel film obtained on the strand. The force required therefore is determined in N by means of a load cell.

Determination of the curl retention C.R. of a strand treated with a composition of the invention:

A gel as indicated above containing a copolymer of the invention was prepared and a sufficient amount of said hair styling composition was applied onto a glass plate. By means of a spatula the gel was also spread over a hair strand in a way to uniformly saturate said strand previously washed and dried with the composition. Excess gel was squeezed out and combed out. The strand having a length L of 15.5 cm was then wound on a Teflon® rod having a diameter of 12 mm and fixed thereto by means of filter paper and elastics. The fixed strand was then dried over night at a temperature ranging from 60° C. to 70° C.

The strand supplemented rod was cooled down for 30 min. and at room temperature the curl obtained was carefully removed therefrom in order to avoid the gel film formed thereon to break. The curl was suspended and the curl length L0 measured. Thereafter the curl was placed in a climatic chamber having a temperature of 25° C. and a relative humidity of 90%. The curl length Lti was determined after 15, 30, 60 and 90 min. as well as after 2, 3, 4, 5 and 24 h of incubation in said climatic chamber. Length measures were realized for 5 strands respectively and mean values Lt obtained after 5 h were used to determine the curl retention using the following equation:

$$\text{Curl-retention C.R. in \%} = (L-Lt)/(L-L0) \times 100$$

Below embodiments of the copolymer of the invention are shown which partially match with those shown in Table 1. However, for the additional embodiments no mechanical data were recorded.

TABLE 2

| Exp. No | 1.(Meth) Acrylat | (Meth) Acrylamid | MAS | $C_{16-18}$-(EO)-MA AS M.-Gemisch | UMA- M.- Gemisch | PETAE P 6661-O |
|---|---|---|---|---|---|---|
| part 1 |||||||
| 01 | EA 51.9 | MMA (6) | — | 40 | — P.-6877-O 4 (1) | P.-6844-O 4 (1) | 0.1 |
| 02 | EA 47.93 | MMA (9) | — | 40 | — P.-6877-O 8 (2) | P.-6844-O 4 (1) | 0.07 |
| 03 | EA 47.9 | MMA (9) | — | 40 | — P.-6877-O 8 (2) | P.-6844-O 4 (1) | 0.1 |
| 04 | EA 47.87 | MMA (9) | — | 40 | — P.-6877-O 8 (2) | P.-6844-O 4 (1) | 0.13 |
| 05 | EA 47.8 | MMA (9) | — | 40 | — P.-6877-O 8 (2) | P.-6844-O 4 (1) | 0.2 |
| 06 | EA 47.7 | MMA (9) | — | 40 | — P.-6877-O 8 (2) | P.-6844-O 4 (1) | 0.3 |
| 07 | EA 47.9 | MMA (9) | — | 40 | — P.-6877-O 8 (2) | P.-6844-O 4 (1) | 0.1 |
| 08 | EA 51.8 | MMA (6) | — | 40 | — P.-6877-O 4 (1) | P.-6844-O 4 (1) | 0.2 |
| 09 | EA 47.8 | MMA (9) | — | 40 | — P.-6877-O 4 (1) | P.-6844-O 8 (2) | 0.2 |
| 10 | EA 42.9 | MMA (9) | — | 45 | — P.-6877-O 8 (2) | P.-6844-O 4 (1) | 0.1 |
| 11 | EA 43.9 | MMA (12) | — | 40 | — P.-6877-O 12 (3) | P.-6844-O 4 (1) | 0.1 |
| part 2 |||||||
| 12 | EA 39.9 | MMA (15) | — | 40 | — P.-6877-O 12 (3) | P.-6844-O 8 (2) | 0.1 |
| 13 | EA 34.9 | MMA (15) | — | 45 | — P.-6877-O 12 (3) | P.-6844-O 8 (2) | 0.1 |
| 14 | EA 46.9 | MMA (6) | — | 40 | 5 P.-6877-O 4 (1) | P.-6844-O 4 (1) | 0.1 |
| 15 | EA 42.9 | MMA (9) | — | 40 | 5 P.-6877-O 8 (2) | P.-6844-O 4 (1) | 0.1 |
| 16 | EA 34.9 | MMA (15) | — | 40 | 5 P.-6877-O 12 (3) | P.-6844-O 8 (2) | 0.1 |
| 17 | EA 40 | MMA (6) | — | 40 | 5 P.-6877-O 8 (2) | UR-A-6.9 | 0.1 |
| 18 | EA 40 | MMA (6) | — | 40 | 5 P.-6877-O 8 (2) | UR-MA---6.9 | 0.1 |
| 19 | EA 45.7 | MMA (6) | NTBAM-12 | 30 (32) | — 6877-O 8 (2) Lutencryl 4 (2) | — | 0.1 0.2* |
| 20 | EA 45.8 | MMA (6) | NTBAM-12 | 30 (32) | — 6877-O 8 (2) Lutencryl 4 (2) | — | — 0.2* |

TABLE 2-continued

| Exp. No | 1.(Meth) Acrylat | (Meth) Acrylamid | MAS | AS | $C_{16-18}$-(EO)-MA M.-Gemisch | UMA- M.- Gemisch | PETAE P 6661-O |
|---|---|---|---|---|---|---|---|
| 21 | EA 46.7 | MAM 10 | 40 (41.6) | — | Lutencryl 3.2 (1.6) | — | 0.1 |
| 32 | EA 44 | NTBAM 14 | 40 (40.5) | — | P.-6954-O tq 2.5 [=2] (1.5) | — | — |
| 33 | EA 45 | NTBAM 14 | 40 (40.25) | — | P.-6954-O tq 1.25 [=1] (0.75) | — | — |
| 34 | EA 38.6 TEA 20 | — | 40 (40.25) | — | P.-6954-O tq 1.25 [=1] (0.75) | P.-6852-O tq 0.8 (=0.4) | — |
| 35 | EA 38.6 EMA 20 | — | 40 (40.25) | — | P.-6954-O tq 1.25 [=1] (0.75) | P.-6852-O tq 0.8 (=0.4) | — |
| 36 | EA 48.6 | NTBAM 10 | 40 (40.25) | — | P.-6954-O tq 1.25 [=1] (0.75) | P.-6852-O tq 0.8 (=0.4) | — |
| 37 | EA 49 | NTBAM 10 | 40 (40.125) | — | P.-6954-O tq 0.625[=0.5] (0.375) | P.-6852-O tq 1 (=0.5) | — |
| 38 | EA 49 | MAM 10 | 40 (40.125) | — | P.-6954-O tq 0.625[=0.5] (0.375) | P.-6852-O tq 1 (=0.5) | — |
| 40 | EA 49 | NTBAM 10 | 40 (40.25) | — | P.-6954-O tq 1.25 [=1] (0.75) | — | — |
| 41 | EA 48 | NTBAM 10 | 40 (40.5) | — | P.-6954-O tq 2.5 [=2] (1.5) | — | — |
| 42 | EA 49 | NTBAM 10 | 40 (40.5) | — | Lutencryl 1.0 (0.5) | — | — |
| 43 | EA 49 | NTBAM 10 | 40.25 (40.625) | — | Lutencryl 0.75 (0.375) | — | — |
| 44 | EA 49 | NTBAM 10 | 35.25 (35.625) | 5 | Lutencryl 0.75 (0.375) | — | — |
| 45 | EA 44 | NTBAM 10 | 40.25 (40.625) part 3 | 5 | Lutencryl 0.75 (0.375) | — | — |
| 46 | EA 47 | NTBAM 10 | 40.25 (40.625) | 2 | Lutencryl 0.75 (0.375) | — | — |
| 47 | EA 44 | MAM 10 | 45 (45.5) | — | Lutencryl 1 (0.5) | — | — |
| 48 | EA 49 | MAM 10 | 40 (40.5) | — | Lutencryl 1 (0.5) | — | — |
| 49 | EA 48.8 | MAM 10 | 40 (40.6) | — | Lutencryl 1.2 (0.6) | — | — |
| 50 | EA 48.5 | MAM 10 | 40 (40.75) | — | Lutencryl 1.5 (0.75) | — | — |
| 61 | EA 46 | NTBAM 10 | 40 (41) | — | P.-6954-O tq 5 [=4] (3) | — | — |
| 62 | EA 45.97 | NTBAM 10 | 40 (41) | — | P.-6954-O tq 5 [=4] (3) | — | 0.03 |

Values without parentheses indicate the amount of metered monomer whereas values in parentheses show the real amount of each monomer used.
The first value for P.-6954 O shown in the table 2 indicates the amount of Plex ®-6954 used, whereas the second numeral in brackets gives the amount of polymerizable monomers within said value and the third numeral in parentheses indicates the amount of macromonomer D within said value.

Different cosmetic or rheological compositions containing the polymer of the invention are disclosed below.

COMPOSITION EXAMPLE 1

[Amounts in w %] INCI (Supplier)

Phase A

| 0.4 Cremophor CO40 | PEG-40 Hydrogenated Castor Oil (BASF SE) |
| 0.1 Perfume oil | |
| 40.0 Water dem. | Aqua dem. |

Phase B

| 0.5 Carbopol ® 980 | Carbomer (Lubrizol Corp.) |
| 0.5 Euxyl PE 9010 | Phenoxyethanol Ethylhexyl Glycerin (Schülke & Mayr GmbH) |
| add 100 Water dem. | Aqua dem. |

Phase C

| 0.7 Triethanolamine Care | Triethanolamine (BASF SE) |

Phase D

| 2.0 GK2391/178 | |
| (6.9 g of polymer emulsion as is) | |
| 1.4 Triethanolamine Care | Triethanolamine (BASF SE) |

Production

The components of phase A were solubilized. The components of phase B were weighed and stirred till homogeneous. Phase B was neutralized with phase C and stirred till homogenous. Phase A was placed into phase B+C and stirred to homogeneity. Phase D was supplemented into the solution of the combined phases A+B+C.

Determined Parameters of the Composition

| Viscosity: | 21.800 mPas | Brookfield RVD VII+ |
| pH value: | 7.0 | |
| Transmission: | 95% at 600 nm | |
| Flexural Strength: | 196 ± 2 cN | |

COMPOSITION EXAMPLE 2

{Amounts in w %} INCI (Supplier)

Phase A

| 0.4 Cremophor CO40 | PEG-40 Hydrogenated Castor Oil (BASF SE) |
| 0.1 Perfume oil | |
| 40.0 Water dem. | Aqua dem. |

Phase B

| 0.5 Carbopol ® Ultrez 21 | Acrylates/C10-30 AlkylAcrylate Crosspolymer (Lubrizol Corp.) |
| 0.5 Euxyl PE 9010 | Phenoxyethanol Ethylhexyl Glycerin (Schülke & Mayr GmbH) |
| add 100 Water dem. | Aqua dem. |

-continued

Phase C

| 0.7 Triethanolamine Care | Triethanolamine (BASF SE) |
|---|---|

Phase D

| 2.0 GK2391/178 | |
| (6.9 g of polymer emulsion as is) | |
| 1.4 Triethanolamine Care | Triethanolamine (BASF SE) |

Production

The components of phase A were solubilized. The components of phase B were stirred till homogeneity. Phase B was neutralized with phase C and stirred till homogeneity.

Phase A was weighed into phase B+C and stirred till homogeneity. Phase D was added to the solution of the combined phases A+B+C and stirred till homogeneity.

Determined Parameters of the Composition

| Viscosity: | 33.900 mPas | Brookfield RVD VII+ |
|---|---|---|
| pH value: | 6.9 | |
| Transmission: | 98% at 600 nm | |
| Flexural strength: | 188 ± 9 cN | |

COMPOSITION EXAMPLE 3

[Amount in w %] INCI (Supplier)

Phase A

| 0.4 Cremophor CO40 | PEG-40 Hydrogenated Castor Oil (BASF SE) |
|---|---|
| 0.1 Perfume oil | |
| 40.0 Water dem. | Aqua dem. |

Phase B

| 2.0 Luviset Clear | VP/Methacrylamide/N-Vinyl-Imidazole Copolymer (BASF SE) |
|---|---|

Phase C

| 0.5 Ultrez 21 | Acrylates/C10-30 AlkylAcrylate Crosspolymer (Lubrizol Corp.) |
|---|---|
| 0.5 Euxyl PE 9010 | Phenoxyethanol Ethylhexyl Glycerin (Schülke & Mayr GmbH) |
| add 100 Water dem. | Aqua dem. |

Phase D

| 0.7 Triethanolamine Care | Triethanolamine (BASF SE) |
|---|---|

Phase E

| 1.0 GK2391/178 (3.45 g | |
| of polymer emulsion as is) | |
| 0.7 Triethanolamine Care | Triethanolamine (BASF SE) |

Production

The components of phase A were solubilized. The component of phase B was weighed into phase A and stirred till homogenous. The components of phase C were weighed and stirred till homogenous. Phase C was neutralized with phase D and stirred till homogenous. Phase A and B were subjected to phase C and D and stirred till homogeneity. Phase E was placed into the solution of the combined phases A+B+C+D and stirred till homogeneity.

Parameters Determined

| Viscosity: | 24.050 mPas | Brookfield RVD VII+ |
|---|---|---|
| PH value: | 7.1 | |
| Transmission: | 94% at 600 nm | |
| Flexural strength: | 246 ± 13 cN | |

COMPOSITION EXAMPLE 4

[Amount in w %] INCI (Supplier)

Phase A

| 0.4 Cremophor CO40 | PEG-40 Hydrogenated Castor Oil (BASF SE) |
|---|---|
| 0.1 Perfume oil | |
| 40.0 Water dem. | Aqua dem. |

Phase B

| 2.0 Propylene glycol care | 1,2-Proyplene glykol (BASF SE) |
|---|---|

Phase C

| 0.5 Carbopol ® 980 | Carbomer (Lubrizol Corp.) |
|---|---|
| 0.5 Euxyl PE 9010 | Phenoxyethanol Ethylhexyl Glycerin (Schülke & Mayr GmbH) |
| add 100 Water dem. | Aqua dem. |

Phase D

| 0.7 Triethanolamine Care | Triethanolamine (BASF SE) |
|---|---|

Phase E

| 2.0 GK2391/178 | |
| (6.9 g of polymer emulsion as is) | |
| 1.4 Triethanolamine Care | Triethanolamine (BASF SE) |

Production

The components of phase A were solubilized. The component of phase B was weighed into phase A and stirred till homogeneity. Phase C was neutralized with phase D and stirred till homogeneity. Phase A and phase B were placed into phase C and D and stirred till homogeneity. Phase E was placed into the solution of the combined phases A+B+C+D with stirring.

Parameters Determined

| Viscosity: | 18.950 mPas | Brookfield RVD VII+ |
|---|---|---|
| pH value: | 6.9 | |
| Transmission: | 96% at 600 nm | |

One realizes that the invention relates to a polymer suited for modifying the styling performance and the rheology of a cosmetic preparation, a composition thereof, a method of making it as well as the use of said polymer and the composition respectively. The copolymer comprises at least one non-ionic ethylenically unsaturated C1-C4 (meth)acrylate as monomer A; an ethylenically unsaturated monomer B having as hydrogen bond donor an amide group, said ethylenically unsaturated monomer B being an ethylenically unsaturated monomer having a cyclic amide moiety, as monomer B1 and/or, an ethylenically unsaturated monomer having an acyclic amide group, as monomer B2; at least one ethylenically unsaturated carboxylic acid as monomer C; a macromonomer D; optionally at least one cross-linker E; and optionally at least one further monomer F.

The invention claimed is:

1. A copolymer for rheological or cosmetic compositions comprising:

a) 15 to 60 w % of at least one non-ionic ethylenically unsaturated C1-C4 (meth)acrylate as monomer A;
b) 0.1 to 30 w % of an ethylenically unsaturated monomer B having as hydrogen bond donor an amide group, said ethylenically unsaturated monomer B being
  b1) 0.0 to 2 w % of an ethylenically unsaturated monomer having a cyclic amide moiety, as monomer B1 and/or,
  b2) 0.0 to 30 w % of an ethylenically unsaturated monomer having an acyclic amide group, as monomer B2, with the sum of monomers B1 and B2 being at least 0.1 w %;
c) 30 to 60 w % of at least one ethylenically unsaturated carboxylic acid as monomer C selected from the group consisting of methacrylic acid, acrylic acid and itaconic acid with methacrylic acid making 80 to 100 w % of said monomer C;
d) 0.1 to 10 w % of a macromonomer D;
e) 0 to 0.3 w % of at least one cross-linker E;
f) 0 to 30 w % of at least one further monomer F selected from the group consisting of ethylenically unsaturated cationogenic or cationic monomers and ethylenically unsaturated sulfonic- or phosphonic acids;
the sum of the compounds A to F equals 100 w %,
with monomer B1 making from $\frac{1}{6}$ to 3.45 times the weight amount of the macromonomer D, and/or
the weight amount of the monomer B2 being at least three times higher than the weight amount of the macromonomer D; wherein macromonomer D comprises, an ethylenically unsaturated oxyalkylated monomer having the general formula (I):

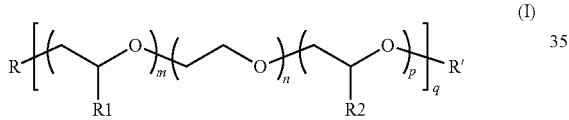

with:
  m and p having a numeral of less than or equal to 50;
  n having a numeral ranging from 1 to 50;
  q being a numeral ranging from 1 to 5
  with the proviso that
  $(m+n+p) \times q \leq 90$;
  R1 representing hydrogen or methyl;
  R2 being hydrogen or methyl;
  R being a polymerizable unsaturated moiety selected from the group consisting of:

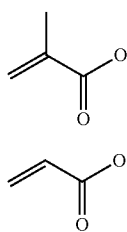

maleic, itaconic, crotonic and vinylphthalic with the oxygen radical thereof making the bond and
R' representing a hydrophobic moiety selected from linear or branched alkyl, alkylaryl or arylalkyl radicals.

2. The copolymer according to claim 1, wherein the monomer A is selected from the group consisting of ethylacrylate, ethylmethacrylate, methylmethacrylate and tert-butylacrylate or any combination thereof with ethylacrylate being the only or the predominant component of monomer A.

3. The copolymer according to claim 1, wherein the monomer B1 makes from $\frac{1}{3}$ to 2 times the weight amount of the macromonomer D.

4. The copolymer according to claim 1, wherein the weight amount of the monomer B1 is at least 24.95 times smaller than that of the non-ionic monomer A.

5. The copolymer according to claim 1, wherein the weight amount of the monomer B2 is at least 6.25 times higher than the amount of the macromonomer D.

6. The copolymer according to claim 1, wherein the weight amount of the sum of the monomer B1 and macromonomer D, or of macromonomer D alone is at least 8 times smaller than the weight amount of monomer C used.

7. The copolymer according to claim 1, wherein it comprises
  a) 44 to 49 w % of monomer A;
    b1) 0.5 to 1 w % of monomer B1 or
    b2) 0.5 to 1 w % of monomer B1 and 10 to 14 w % of monomer B2 or 10 to 14 w % of monomer B2 only, with the sum of monomers B1 and B2 being at least 0.5 w %;
  c) 40.125 to 45.625 w % of monomer C;
  d) 0.375 to 0.5 w % of the macromonomer D;
  e) 0 to 0.2 w % of at least one cross-linker E.

8. The copolymer according to claim 1, wherein
  a) monomer A is ethylacrylate or a mixture of ethylacrylate and methylmethacrylate;
  b1) the monomer B1 is absent or N-(2-Methacryloyloxyethyl)-ethylene urea (UMA) and methylmethacrylate (MMA) in the weight ratio of [25:75] or N-(2-Methacryloyloxyethyl)-ethylene urea (UMA) and H$_2$O in the weight ratio of [50:50];
  b2) monomer B2 is N-tert-butylacrylamide or methacrylamide or a mixture thereof;
  c) monomer C is methacrylic acid or a mixture of methacrylic acid and acrylic acid;
  d) monomer D is C$_{16-18}$-Alkyl (EO)$_{25}$-Methacrylate (MA), Methacrylic Acid (MAS) and H$_2$O in the weight ratio of [60/20/20] or C$_{16-18}$-Alkyl (EO)$_{25}$-MA and MAS in the weight ratio of [50:50] or for C$_{16-18}$-Alkyl (EO)$_{25}$-MA and MMA in the weight ratio of [25:75] or a mixture of two or three of the previously mentioned compounds;
  e) monomer E is absent or pentaerythritoltriallylether or Diurethane-dimethacrylate or a mixture thereof.

9. A composition comprising
  as component A the copolymer of claim 1;
  as component B at least one cosmetically or pharmaceutically acceptable carrier selected from the group consisting of
    i) water,
    ii) water-miscible organic solvents,
    iii) oils, fats, waxes,
    iv) esters of C6-C30-monocarboxylic acids with mono-, di- or trihydric alcohols which are different from iii),
    v) saturated acyclic and cyclic hydrocarbons,
    vi) fatty acids,
    vii) fatty alcohols,
    viii) propellant gases
    and mixtures thereof.

10. The composition according to claim 9, comprising at least one additive different from components A) and B) selected from the group consisting of cosmetically active ingredients, emulsifiers, surfactants, preservatives, perfume oils, thickeners, hair polymers, hair and skin conditioners, graft polymers, water-soluble or dispersible silicone-containing polymers, photoprotective agents, bleaches, gel formers, care agents, colorants, tinting agents, tanning agents, dyes, pigments, bodying agents, humectants, regreasing agents, collagen, protein hydrolyzates, lipids, antioxidants, antifoams, antistats, emollients and softeners.

11. The composition according to claim 9 in the form of a liquid, gel, foam, spray, mousse, spritz, ointment, cream, emulsion, suspension, lotion, milk, solid or semisolid or paste.

12. A process for preparing the copolymer according to claim 1, the process comprising:
   a) preparing an aqueous solution containing between 2 and 10 w % of a mixture containing monomers of the copolymer of claim 1 under stirring;
   b) heating the aqueous solution up to a temperature ranging from 30° C. to 60° C. under nitrogen with stirring;
   c) adding to the aqueous solution an aliquot of at least one polymerization initiator with stirring and heating to a reaction temperature ranging from 70° C. to 100° C. to form a polymerization reaction mixture;
   d) supplementing the polymerization reaction mixture of step c) with the remaining 90-98 w % of the mixture containing monomers of the copolymer of claim 1 of step a) over a time period ranging from 0.5 to 4 hours;
   e) adding the residual polymerization initiator of step c) during the course of step d);
   f) thereafter maintaining the reaction temperature for another 0.5 to 2 hours, followed by cooling to 40° C. to 60° C.; and
   g) adding a mixture of an oxidizing agent and a radical scavenger over a time period ranging from 15 min to 2 hours.

13. The process according to claim 12, wherein the copolymer is prepared by emulsion polymerization in water.

14. The copolymer of claim 1, wherein the copolymer is prepared by emulsion polymerization in water.

* * * * *